United States Patent
Honjo et al.

(10) Patent No.: US 11,651,485 B2
(45) Date of Patent: May 16, 2023

(54) MEDICAL IMAGE PROCESSING APPARATUS, TRAINING DATA PRODUCING APPARATUS, AND ULTRASOUND DIAGNOSIS APPARATUS

(71) Applicant: Canon Medical Systems Corporation, Otawara (JP)

(72) Inventors: Yasunori Honjo, Utsunomiya (JP); Keita Yonemori, Utsunomiya (JP); Masaki Watanabe, Utsunomiya (JP); Yuko Takada, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 204 days.

(21) Appl. No.: 16/818,764

(22) Filed: Mar. 13, 2020

(65) Prior Publication Data

US 2020/0294230 A1    Sep. 17, 2020

(30) Foreign Application Priority Data

Mar. 14, 2019    (JP) .............................. JP2019-047348

(51) Int. Cl.
*G06T 7/00*    (2017.01)
*G06N 20/00*   (2019.01)
*A61B 8/00*    (2006.01)

(52) U.S. Cl.
CPC .......... *G06T 7/0012* (2013.01); *A61B 8/4444* (2013.01); *G06N 20/00* (2019.01);
(Continued)

(58) Field of Classification Search
CPC ......... G06T 7/0012; G06T 2207/30004; G06T 2207/20081; G06T 2207/20084;
(Continued)

(56) References Cited

U.S. PATENT DOCUMENTS 6,312,386 B1 *   11/2001   Bolorforosh .......... G10K 11/346
                                                    600/447
2011/0060223 A1 *  3/2011  Kim ..................... G01S 7/52063
                                                    600/443
(Continued)

FOREIGN PATENT DOCUMENTS

JP    H0530355 A    2/1993
JP    H08-153194 A  6/1996
(Continued)

OTHER PUBLICATIONS

Office Action dated Nov. 15, 2022 in Japanese Application No. 2019-047348.
(Continued)

*Primary Examiner* — Van D Huynh
(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry acquires an input image based on reception data collected by transmitting/receiving ultrasound by using an ultrasound probe including a plurality of vibration elements driven in accordance with a delay profile, stores a plurality of trained models for generating, based on an input image, an output image in which noise is reduced according to a wavefront shape of when the ultrasound is transmitted in an input image, selects a trained model corresponding to a type of the ultrasound probe or the delay profile from the plurality of trained models, and generates an output image by inputting an input image to the selected trained model.

8 Claims, 16 Drawing Sheets

(52) U.S. Cl.
CPC .............. *G06T 2207/10132* (2013.01); *G06T 2207/20081* (2013.01); *G06T 2207/20084* (2013.01); *G06T 2207/20182* (2013.01); *G06T 2207/30004* (2013.01)

(58) Field of Classification Search
CPC . G06T 2207/10132; G06T 2207/20182; G06T 5/001; G06N 20/00; G06N 3/0454; A61B 8/4444; A61B 8/5269; G01S 7/52077
USPC ......................................................... 382/156
See application file for complete search history.

(56) References Cited

U.S. PATENT DOCUMENTS

| | | | |
|---|---|---|---|
| 2014/0121524 A1* | 5/2014 | Chiang | A61B 8/0891 600/459 |
| 2014/0187953 A1* | 7/2014 | Miyachi | G01S 7/52049 600/447 |
| 2018/0129782 A1* | 5/2018 | Himsl | G16H 30/20 |
| 2018/0177461 A1* | 6/2018 | Bell | G06T 5/002 |
| 2018/0214134 A1* | 8/2018 | Kim | A61B 8/4405 |
| 2020/0234461 A1* | 7/2020 | Osumi | G06T 7/62 |
| 2020/0245969 A1* | 8/2020 | Tung | A61B 8/5207 |

FOREIGN PATENT DOCUMENTS

| | | |
|---|---|---|
| JP | 2016-531709 A | 10/2016 |
| JP | 2017-055845 A | 3/2017 |
| JP | 2017-058930 A | 3/2017 |
| JP | 2018-122082 A | 8/2018 |
| JP | 2018-206382 A | 12/2018 |

OTHER PUBLICATIONS

Office Action dated Feb. 14, 2023, in Japanese Patent Application No. 2019-047348 filed Mar. 14, 2019, 4 pages.

* cited by examiner

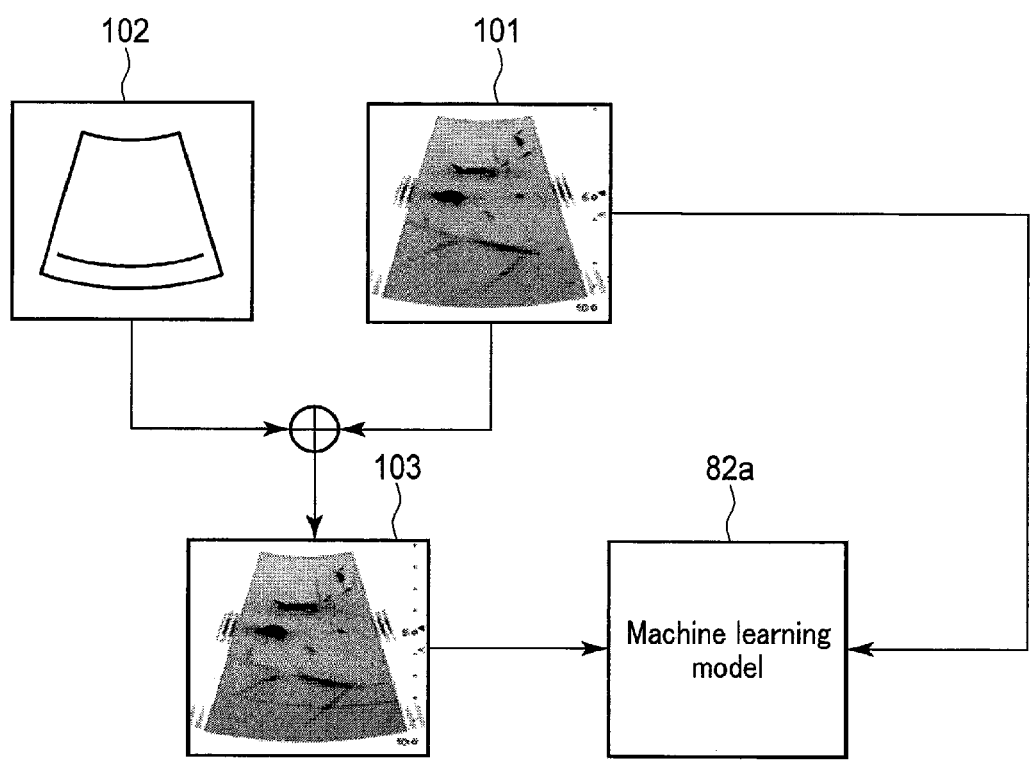
F I G. 10

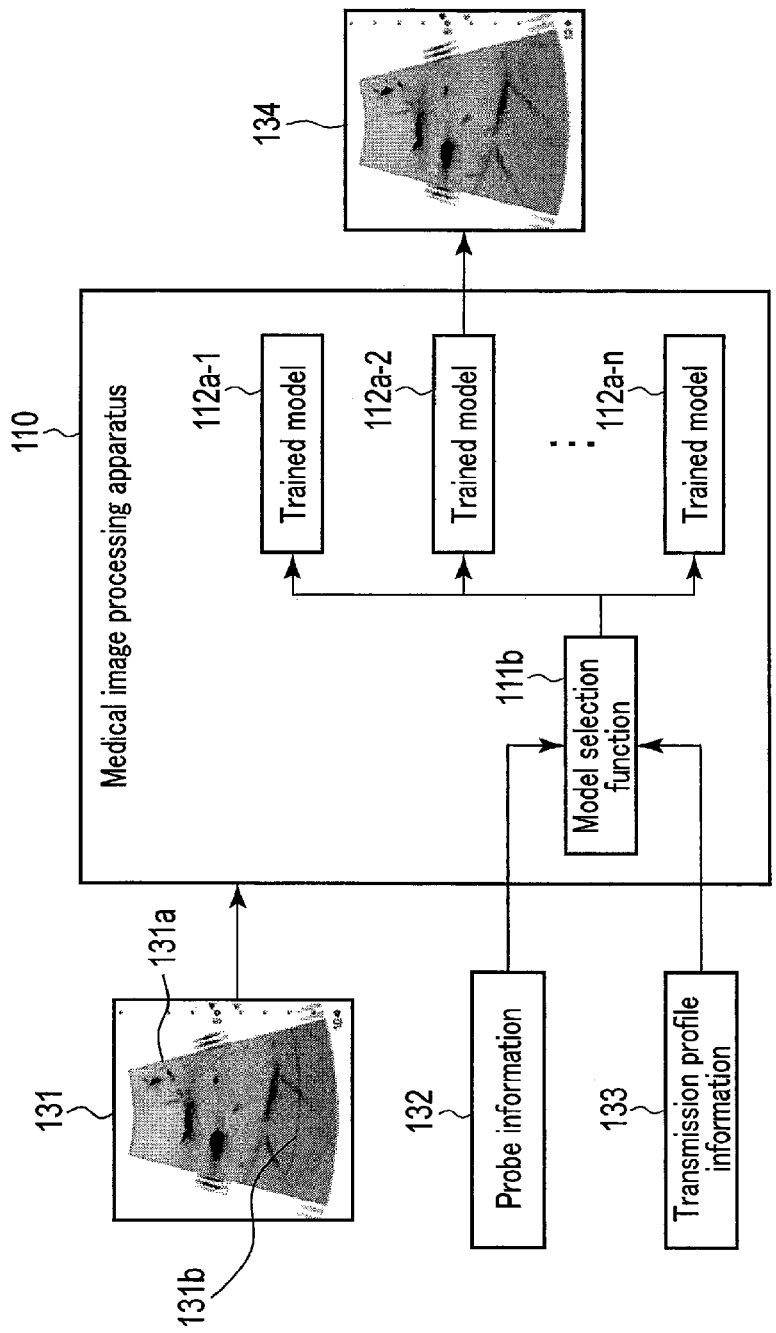
F I G. 13

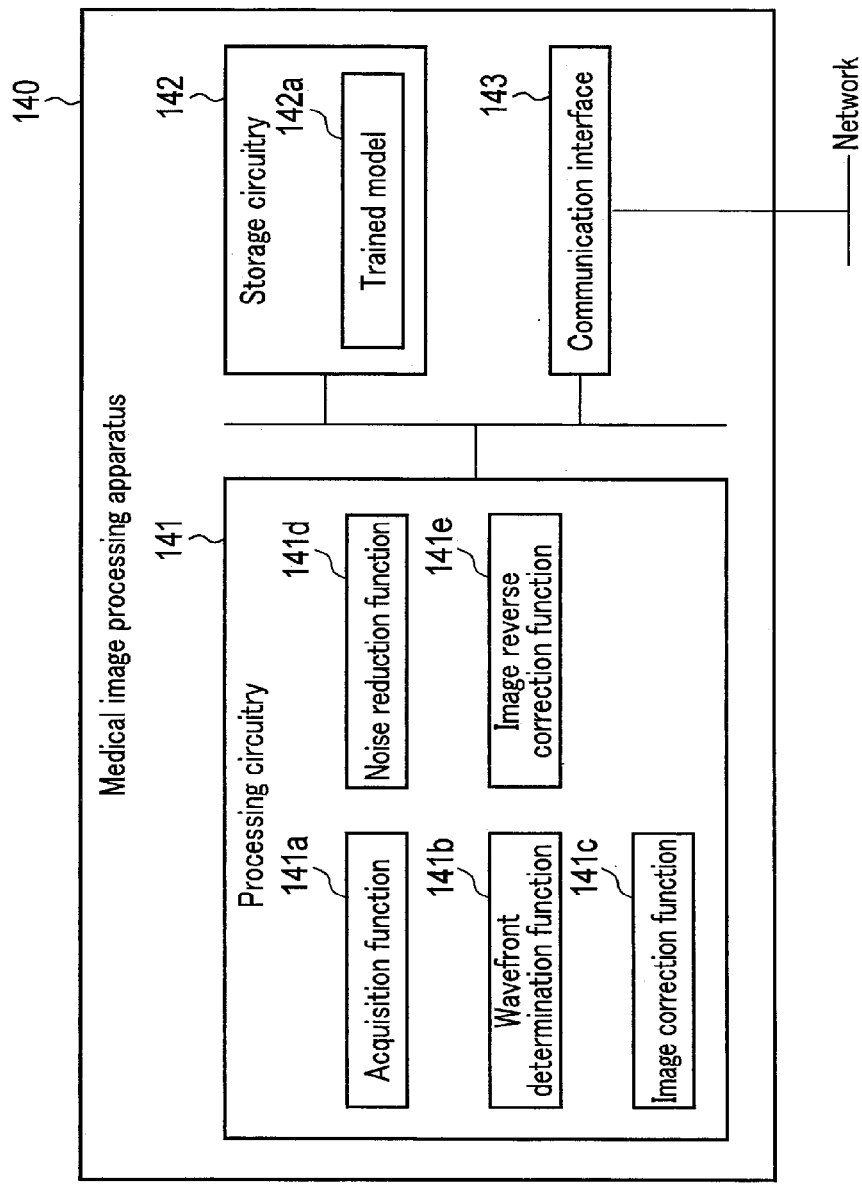
F I G. 14

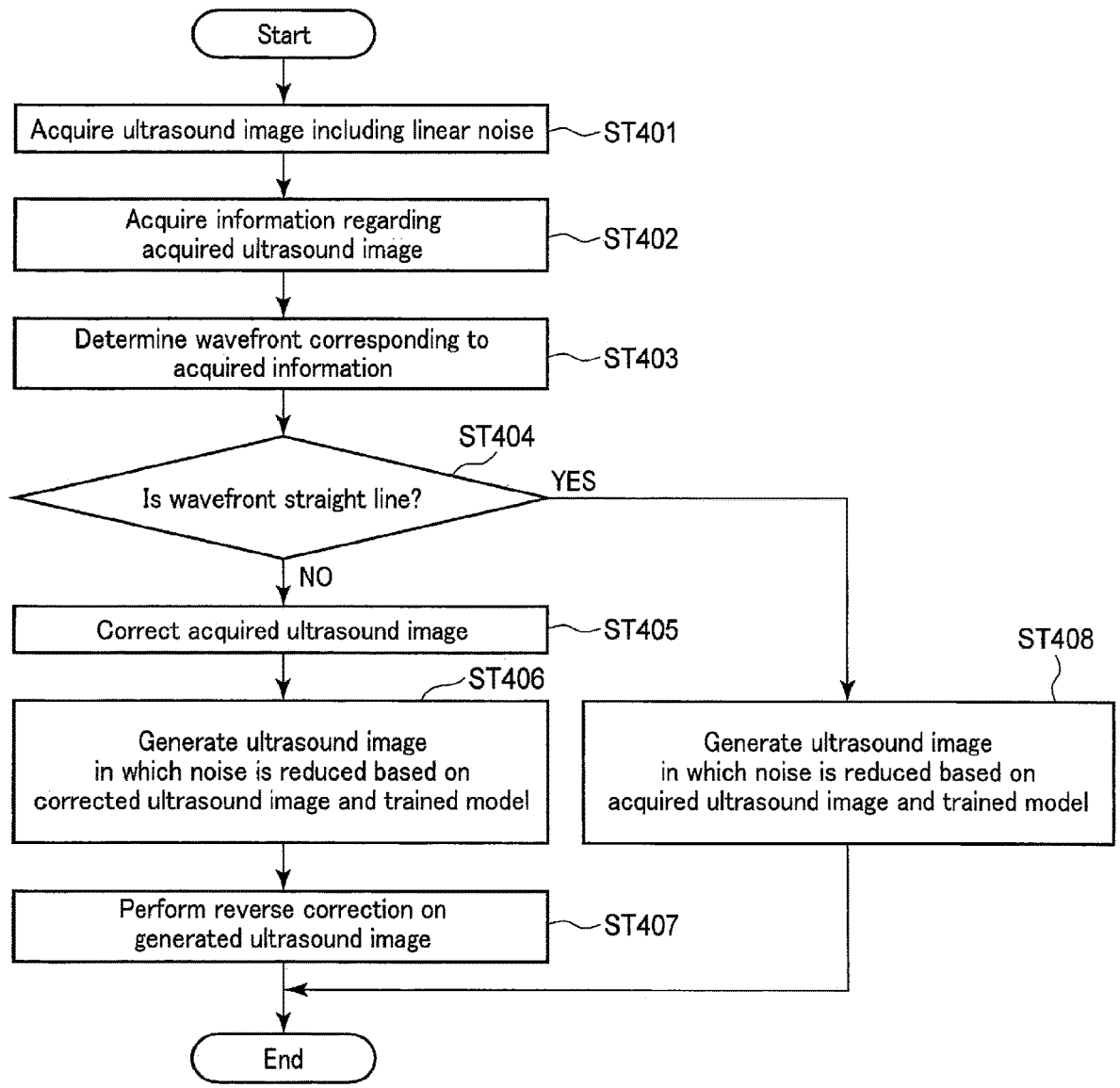
F I G. 15

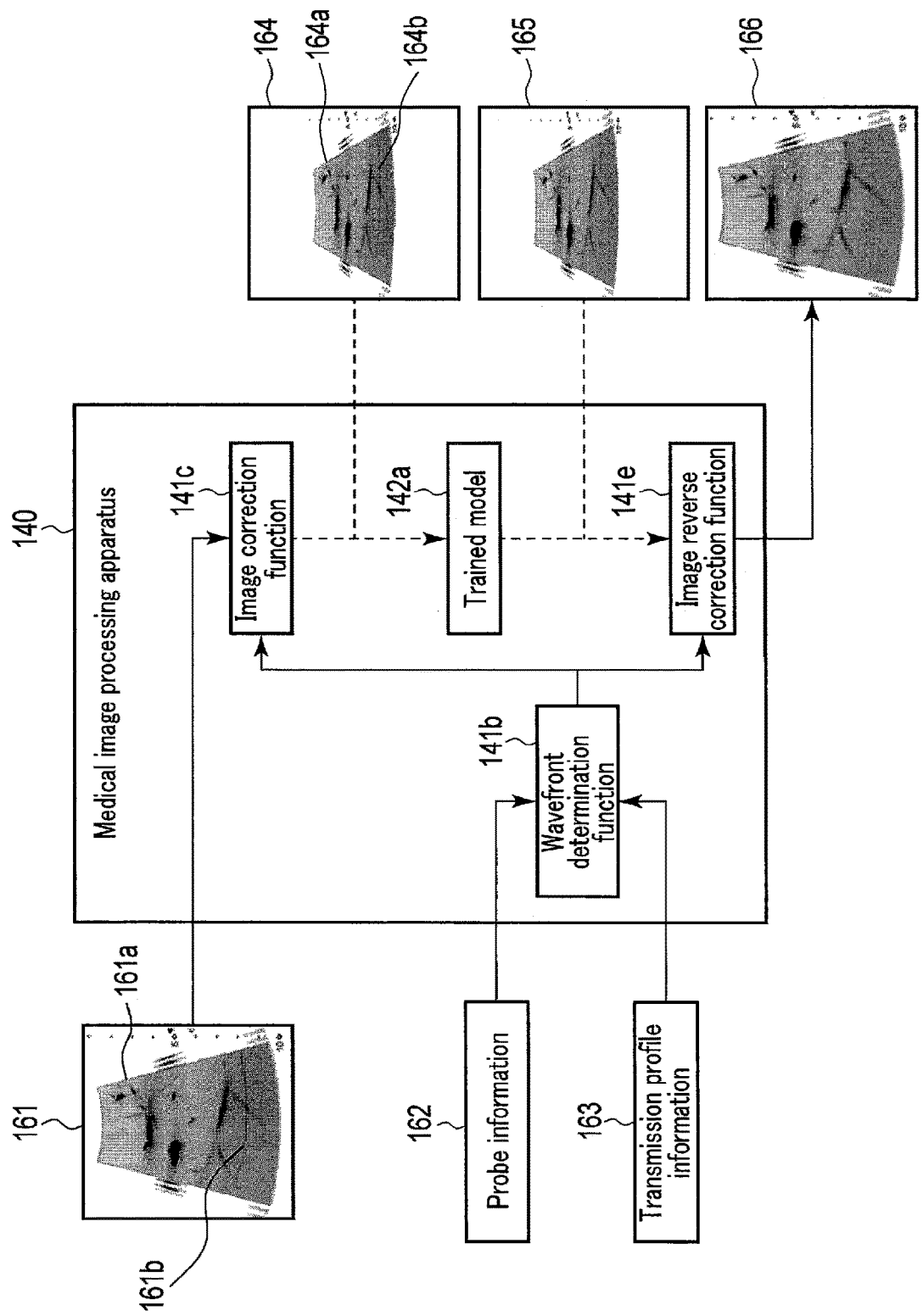
F I G. 16

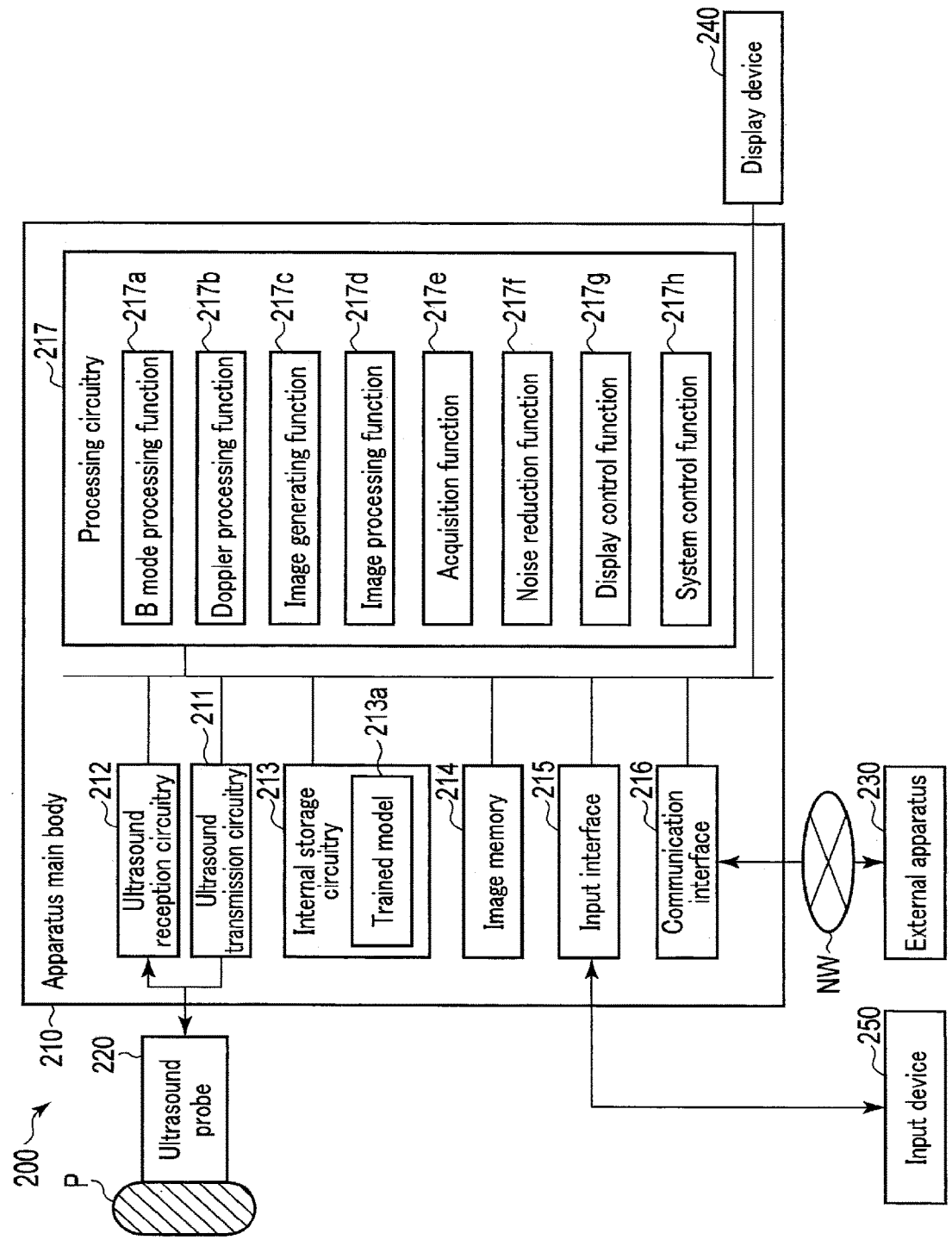
F I G. 20

MEDICAL IMAGE PROCESSING APPARATUS, TRAINING DATA PRODUCING APPARATUS, AND ULTRASOUND DIAGNOSIS APPARATUS

CROSS-REFERENCE TO RELATED APPLICATIONS

This application is based upon and claims the benefit of priority from Japanese Patent Application No. 2019-047348, filed Mar. 14, 2019, the entire contents of which are incorporated herein by reference.

FIELD

Embodiments described herein relate generally to a medical image processing apparatus, a training data producing apparatus, and an ultrasound diagnosis apparatus.

BACKGROUND

In recent years, an ultrasound diagnosis apparatus has been known for its technique of improved temporal resolution by performing plane wave transmission or diffusion wave transmission. For example, such technique is utilized not only for displaying a B mode image, but also for various scenes, such as for speckle tracking with respect to a tracking pulse and blood flow of shear wave elastography (SWE).

In an ultrasound image generated by using a plane wave or a diffusion wave as a transmission wave, in some cases, saturation attributable to a high echo region may cause straight linear noise or arcuate noise to occur. That is, such noise may occur in accordance with a wavefront shape of the transmission wave. Such noise may also occur by a focusing wave.

BRIEF DESCRIPTION OF THE DRAWINGS

FIG. 10 is a drawing schematically showing an operation of the model learning apparatus according to the second embodiment.

FIG. 13 is a drawing schematically showing an operation of the medical image processing apparatus according to the third embodiment.

FIG. 14 is a block diagram showing a configuration example of a medical image processing apparatus according to a fourth embodiment.

FIG. 15 is a flowchart explaining an operation of the medical image processing apparatus according to the fourth embodiment.

FIG. 16 is a drawing schematically showing an operation of the medical image processing apparatus according to the fourth embodiment.

FIG. 20 is a block diagram showing a configuration example of an ultrasound diagnosis apparatus according to a sixth embodiment.

DETAILED DESCRIPTION

In general, according to one embodiment, a medical image processing apparatus includes processing circuitry. The processing circuitry acquires an input image based on reception data collected by transmitting/receiving ultrasound by using an ultrasound probe including a plurality of vibration elements driven in accordance with a delay profile, stores a plurality of trained models for generating, based on an input image, an output image in which noise is reduced according to a wavefront shape of when the ultrasound is transmitted in an input image, selects a trained model corresponding to a type of the ultrasound probe or the delay profile from the plurality of trained models, and generates an output image by inputting an input image to the selected trained model.

Embodiments of a medical image processing apparatus, a model learning apparatus, and an ultrasound diagnosis apparatus will be explained below in detail with reference to the drawings.

First Embodiment

Figure 1:
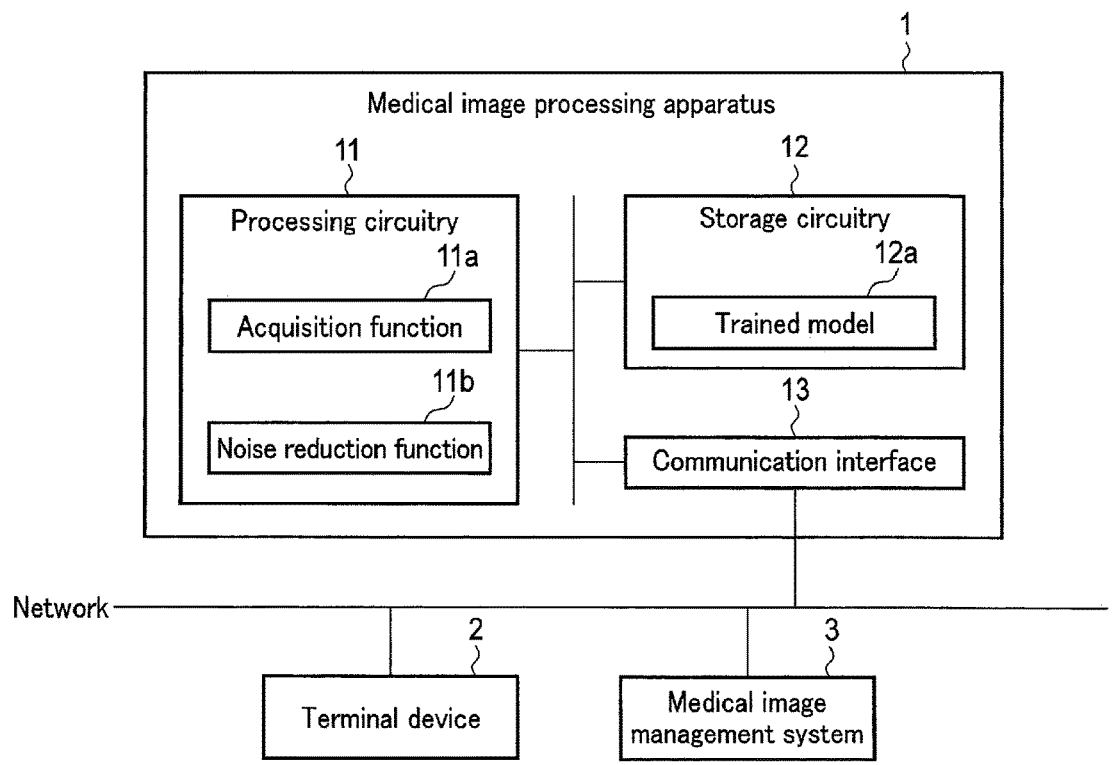
FIG. 1 is a block diagram showing a configuration example of a medical image processing system including a medical image processing apparatus according to a first embodiment.

FIG. 1 is a block diagram showing a configuration example of a medical image processing system including a medical image processing apparatus according to a first embodiment. As shown in FIG. 1, for example, the medical image processing system according to the present embodiment comprises a medical image processing apparatus 1, a terminal device 2, and a medical image management system 3. The medical image processing apparatus 1, the terminal device 2, and the medical image management system 3 are connected to each other via, for example, a network installed in a medical facility. The medical information processing system may comprise a plurality of terminal devices.

The terminal device 2 corresponds to, for example, a personal computer (PC), a tablet type PC, a personal digital assistant (PDA), and a smart phone. The terminal device 2 is arranged in each diagnosis and treatment department in the medical facility. In the terminal device 2, for example, various instructions relating to processing for reducing noise (noise reduction processing) in accordance with the shape of a transmission wave wavefront (wavefront shape) are input by an operator. The terminal device 2 transmits the various input instructions to the medical image processing apparatus 1 or the medical image management system 3. In the explanations hereafter, instructions to the medical image processing apparatus 1 are assumed to be made by an operator operating the terminal device 2.

The medical image management system 3 is configured by, for example, a server device into which a picture archiving and communication system (PACS) is installed. The medical image management system 3 stores, for example, medical image data collected by various medical image diagnostic apparatuses. Specifically, the medical image management system 3 stores an ultrasound image collected by an ultrasound diagnosis apparatus. The medical image management system 3 transmits the ultrasound image to the medical image processing apparatus 1 in accordance with the instruction from the medical image processing apparatus 1 or the instruction from the terminal device 2. The medical image management system 3 may attach probe information and transmission profile information explained later to the ultrasound image. The probe information and the transmission profile information are described, for example, on a unique tag in a digital imaging and communication in medicine (DICOM) standard.

The medical image processing apparatus 1 comprises processing circuitry 11, storage circuitry 12, and a communication interface 13. The medical image processing apparatus 1 is an apparatus that generates an ultrasound image in which noise is reduced by applying, for example, processing using machine learning with respect to an ultrasound image including noise in accordance with a wavefront shape of the transmission wave.

The communication interface 13 is able to use, for example, a network interface card (NIC). The communication interface 13 is, for example, a circuit relating to communications with the terminal device 2 and the medical image management system 3. In the explanations hereafter, the description will be omitted on the communication interface 13 intervening in communications between the medical image processing apparatus 1 and other apparatuses connected to the network.

The storage circuitry 12 is configured by, for example, a memory that records electrical information, such as a hard disk drive (HDD), and peripheral circuitry, such as a memory controller and a memory interface pertaining to the memory. The memory is not limited to an HDD. A solid state drive (SSD), a magnetic disk (a floppy (registered trademark) disk, etc.), an optical disk (CD, DVD, Blu-ray (registered trademark), etc.), and a semiconductor memory can be used as appropriate. The configuration of the storage circuitry is also the same in each embodiment hereinafter.

The storage circuitry 12 stores a system control program of the medical image processing apparatus 1, instructions of an operator transmitted from the terminal device 2, and various data received via the network, etc. Furthermore, the storage circuitry 12 stores a trained model 12a. The storage circuitry 12 may store the trained model 12a in advance of delivery of the medical image processing apparatus 1. Alternatively, the storage circuitry 12 may store the trained model 12a acquired from a server device, etc. (not shown) after the medical image processing apparatus 1 is delivered.

The trained model 12a is a trained machine learning model that is obtained by performing machine learning on a machine learning model in accordance with a model learning program based on training data. Here, the trained model 12a of the present embodiment is provided with a function to output an ultrasound image in which noise is reduced based on an input of an ultrasound image that includes linear noise. In this case, the training data includes input data, which is an ultrasound image including linear noise, and output data, which is an ultrasound image in which the noise is reduced.

The machine learning model according to the present embodiment is a composite function with parameters, in which a plurality of functions are combined, and which, with an ultrasound image including linear noise as the input, outputs an ultrasound image in which the noise is reduced. The composite function with parameters is defined by a combination of a plurality of adjustable functions and parameters. The machine learning model according to the present embodiment may be any composite function with parameters satisfying the above-described requirements, and is assumed to be a multilayer network model (hereinafter referred to as a multi-layered network). The trained model 12a using the multi-layered network includes an input layer to input an ultrasound image having linear noise, an output layer to output the ultrasound image in which the noise is reduced, and an intermediate layer of at least one layer provided between the input layer and the output layer. The trained model 12a is assumed to be used as a program module that is a part of artificial intelligence software.

As the multi-layered network according to the present embodiment, for example, a deep neural network (DNN), which is a multi-layered neural network to be the target of deep learning, is used. As the DNN, for example, a convolution neural network (CNN) targeting an image may be used. The above explanation on the multi-layered network corresponds also to all of the following trained models and machine learning models.

The processing circuitry 11 comprises, as hardware resources, a processor and a memory. The processing circuitry 11 reads a system control program stored in the storage circuitry 12 in accordance with an instruction input by an operator via the terminal device 2. The processing circuitry 11 executes each function relating to the noise reduction processing in accordance with the read system control program. Each of the above functions is, for example, an acquisition function 11a and a noise reduction function 11b. The processing circuitry 11 that executes the acquisition function 11a may be referred to as an "acquisition unit", and the processing circuitry 11 that executes the noise reduction function 11b may be referred to as a "processing unit".

By the acquisition function 11a, the processing circuitry 11 acquires an input image based on reception data collected by transmitting/receiving ultrasound. Specifically, by the acquisition function 11a, the processing circuitry 11 acquires, for example, an ultrasound image including linear noise from the medical image management system 3. The linear noise is assumed as straight linear noise (hereinafter referred to as straight noise) or arcuate noise (hereinafter referred to as arc noise). The processing circuitry 11 may acquire a plurality of ultrasound images obtained by cutting out a dynamic picture image in units of frames. This also applies to each of the following embodiments.

The shape of the above linear noise is attributable to a wavefront shape of the transmission wave That is, the linear noise is similar to the wavefront shape of the transmission wave. The transmission wave in the present embodiment corresponds to a composite wave obtained by combining a plurality of sound waves from a plurality of oscillators included in the probe. The transmission wave is assumed to be a plane wave or a diffusion wave. The plane wave in the present embodiment is, for example, a transmission wave in which the wavefront becomes straight in a scan surface. For example, a plane wave with a zero deflection angle in the case of using a linear probe is a composite wave in the case where each of the plurality of sound waves is generated without delay, or in the case where each of the plurality of sound waves is generated by being delayed by the same delay time. The diffusion wave in the present embodiment is, for example, a transmission wave in which the wavefront becomes arcuate in a scan surface. For example, a diffusion wave with a zero deflection angle in the case of using a linear probe is a composite wave in the case where a sound wave corresponding to an outer oscillator among the plurality of sound waves is generated by being delayed with respect to a sound wave corresponding to an inner oscillator. The transmission wave may include, as a type of diffusion wave, for example, a focusing wave, which is a Gaussian wave approximating a focusing sound field, or an approximate plane wave in which a focal depth is made extremely far. This also applies to the following embodiments.

Figure 2:
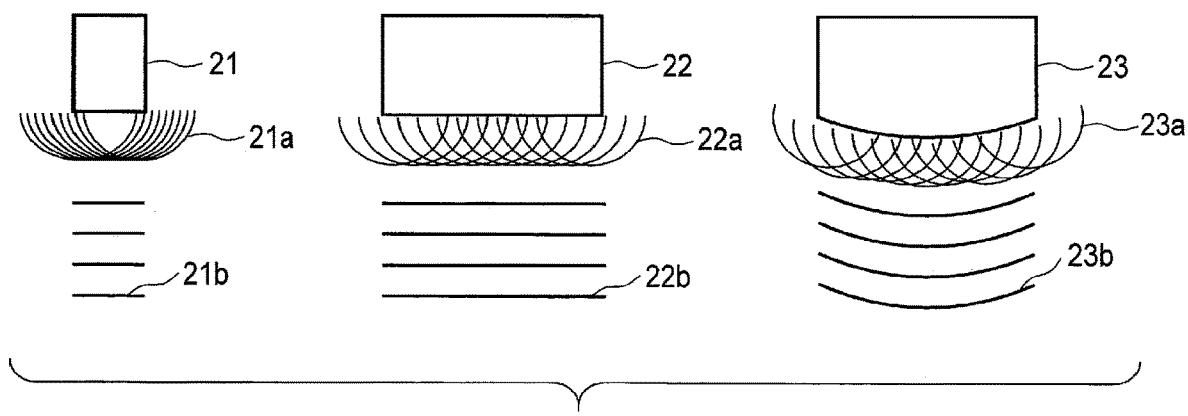
FIG. 2 is a schematic diagram exemplifying a plurality of ultrasound probes in the first embodiment.

FIG. 2 is a schematic diagram exemplifying a plurality of ultrasound probes in the first embodiment. As a plurality of ultrasound probes, a sector probe 21, a linear probe 22, and a convex probe 23 are exemplified. The plurality of probes above include a plurality of oscillators, respectively, and are electronic scan probes that perform electronic scanning.

The sector probe 21 includes a plurality of oscillators arranged linearly. Each of the oscillators of the plurality of oscillators generates a wavefront 21a by ultrasound. For example, the sector probe 21 generates a composite wavefront 21b which is obtained by simultaneously driving a plurality of oscillators and combining wavefronts from each oscillator.

The linear probe 22 includes a plurality of oscillators arranged linearly. Each of the oscillators of the plurality of oscillators generates a wavefront 22a by ultrasound. For example, the linear probe 22 generates a composite wavefront 22b which is obtained by simultaneously driving a plurality of oscillators and combining wavefronts from each oscillator.

The convex probe 23 includes a plurality of oscillators arranged in a curve. Each of the oscillators of the plurality of oscillators generates a wavefront 23a by ultrasound. For example, the convex probe 23 generates a composite wavefront 23b which is obtained by simultaneously driving a plurality of oscillators and combining wavefronts from each oscillator.

In the explanations and drawings hereinafter, a wavefront of a transmission wave is assumed to be formed in a manner corresponding to an opening width in which all of the oscillators are used by each probe. However, the opening width is not limited to the case of using all of the oscillators, and may also be a case of using a part of the oscillators. Specifically, in the linear probe 22 and the convex probe 23, for example, a wavefront of the transmission wave may be formed in a manner corresponding to an opening width in which half of all of the oscillators are used. Furthermore, hereinafter, the description, wavefront, is assumed as being a "composite wavefront".

Figure 3:
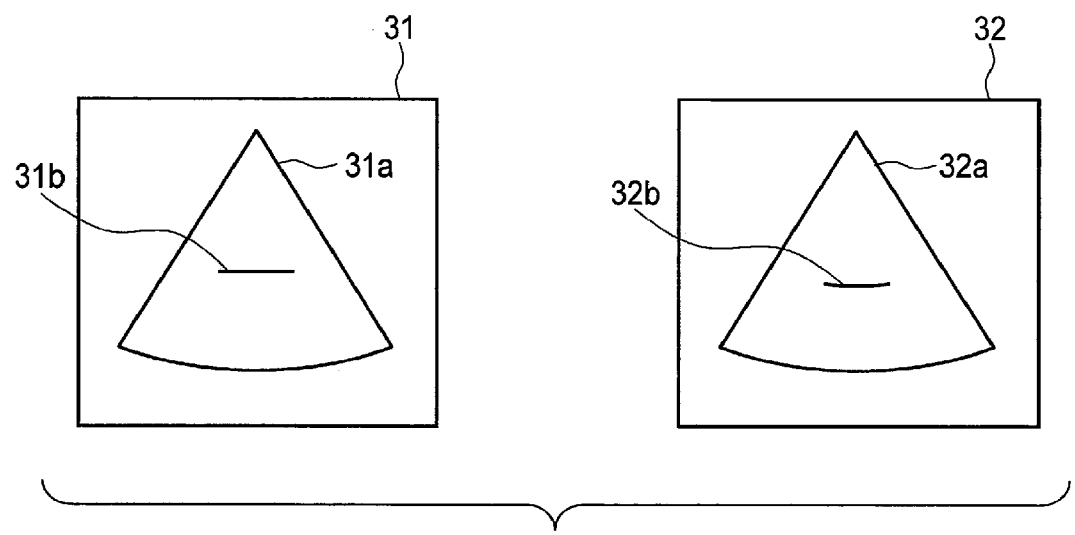
FIG. 3 is a schematic diagram exemplifying an ultrasound image and a wavefront of a transmission wave generated by using a sector probe in the first embodiment.

FIG. 3 is a schematic diagram exemplifying an ultrasound image and a wavefront of a transmission wave generated by using the sector probe in the first embodiment.

In an ultrasound image 31, a wavefront 31b of a transmission wave is shown in a drawing region 31a. The wavefront 31b shows a wavefront of a plane wave in the sector probe. The wavefront 31b may be a cause for straight noise to occur with respect to the ultrasound image.

In an ultrasound image 32, a wavefront 32b of a transmission wave is shown in a drawing region 32a. The wavefront 32b shows a wavefront of a diffusion wave in the sector probe. The wavefront 32b may be a cause for arc noise to occur with respect to the ultrasound image.

Figure 4:
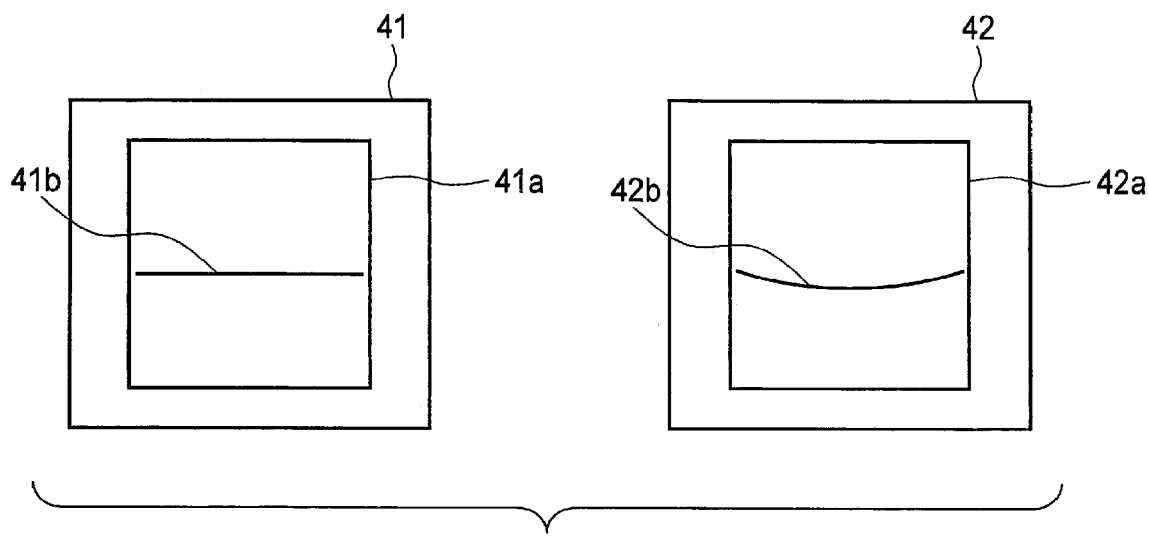
FIG. 4 is a schematic diagram exemplifying an ultrasound image and a wavefront of a transmission wave generated by using a linear probe in the first embodiment.

FIG. 4 is a schematic diagram exemplifying an ultrasound image and a wavefront of a transmission wave generated by using the linear probe in the first embodiment.

In an ultrasound image 41, a wavefront 41b of a transmission wave is shown in a drawing region 41a. The wavefront 41b shows a wavefront of a plane wave in the linear probe. The wavefront 41b may be a cause for straight noise to occur with respect to the ultrasound image.

In an ultrasound image 42, a wavefront 42b of a transmission wave is shown in a drawing region 42a. The wavefront 42b shows a wavefront of a diffusion wave in the linear probe. The wavefront 42b may be a cause for arc noise to occur with respect to the ultrasound image.

Figure 5:
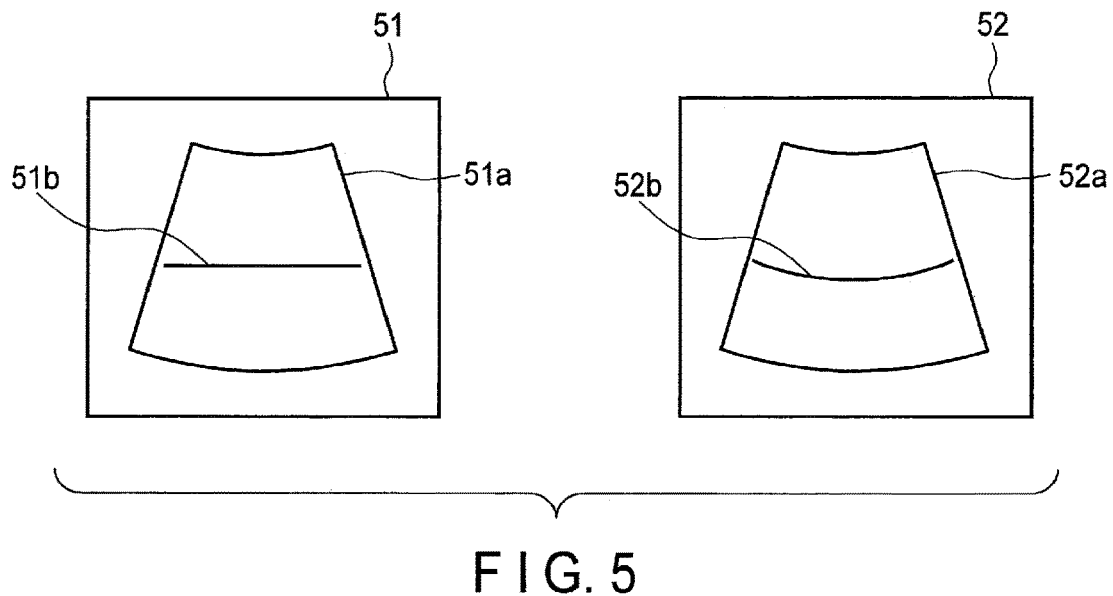
FIG. 5 is a schematic diagram exemplifying an ultrasound image and a wavefront of a transmission wave generated by using a convex probe in the first embodiment.

FIG. 5 is a schematic diagram exemplifying an ultrasound image and a wavefront of a transmission wave generated by using the convex probe in the first embodiment.

In an ultrasound image 51, a wavefront 51b of a transmission wave is shown in a drawing region 51a. The wavefront 51b shows a wavefront of a plane wave in the convex probe. The wavefront 51b may be a cause for straight noise to occur with respect to the ultrasound image.

In an ultrasound image 52, a wavefront 52b of a transmission wave is shown in a drawing region 52a. The wavefront 52b shows a wavefront of a diffusion wave in the convex probe. The wavefront 52b may be a cause for arc noise to occur with respect to the ultrasound image.

By the noise reduction function 11b, the processing circuitry 11 generates an output image by inputting the input image to a trained model for generating, based on an input image, an output image in which noise is reduced according to the wavefront shape of when the ultrasound is transmitted in an input image. Furthermore, since a trained model corresponding to each of a plurality of wavefront shapes may be used, the processing circuitry 11 may also generate an output image by inputting an input image with respect to the trained model according to the wavefront shape.

Specifically, by the noise reduction function 11b, the processing circuitry 11 generates an ultrasound image in which noise is reduced by inputting an ultrasound image including linear noise to a trained model that generates an ultrasound image in which noise is reduced based on the ultrasound image including linear noise. In other words, the processing circuitry 11 generates an ultrasound image in which noise is reduced by inputting an ultrasound image including linear noise to the trained model.

Furthermore, processing circuitry 11 may store the trained model 12a in its own memory, etc. That is, instead of storing a program (a trained model 12a) in the storage circuitry 12, the program may be incorporated directly into circuitry of the processor. In this case, the processor realizes the function by reading and executing the program incorporated into the circuitry. Furthermore, the trained model 12*a* may be implemented on circuits such as an application specific integrated circuit (ASIC) and a field programmable gate array (FPGA). Such circuits may be incorporated into the processing circuitry 11.

Figure 6:
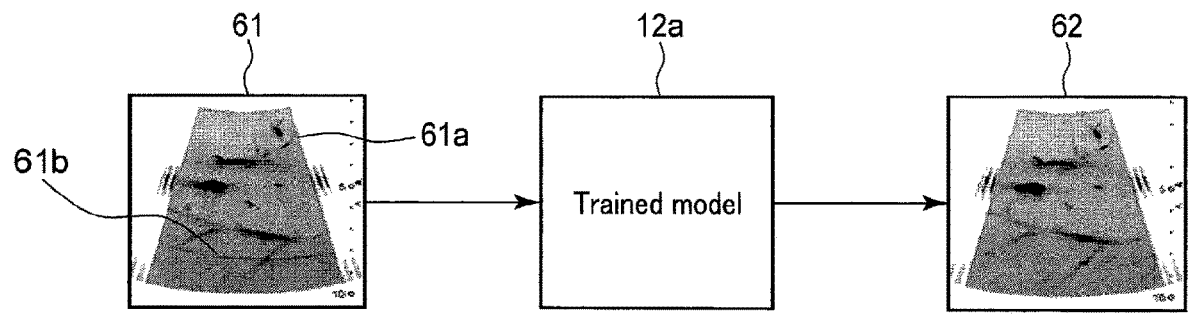
FIG. 6 is a drawing explaining an operation of a trained model to be used in the medical image processing apparatus according to the first embodiment.

FIG. 6 is a drawing explaining an operation of the trained model to be used in the medical image processing apparatus according to the first embodiment. An ultrasound image 61 is acquired by, for example, the convex probe. The ultrasound image 61 has arc noise 61*b* in a drawing region 61*a*. The arc noise 61*b* is similar to, for example, the wavefront 52*b* of FIG. 5, that is, the wavefront shape of the diffusion wave in the convex probe. An ultrasound image 62 is obtained by reducing the arc noise 61*b* in the ultrasound image 61.

For example, the processing circuitry 11 generates the ultrasound image 62 in which the arc noise 61*b* is reduced by inputting the ultrasound image 61 including the arc noise 61*b* to the trained model 12*a*.

The operation of the medical image processing apparatus 1 according to the first embodiment configured in the above manner will now be explained in accordance with the processing procedure of processing circuitry 11.

Figure 7:
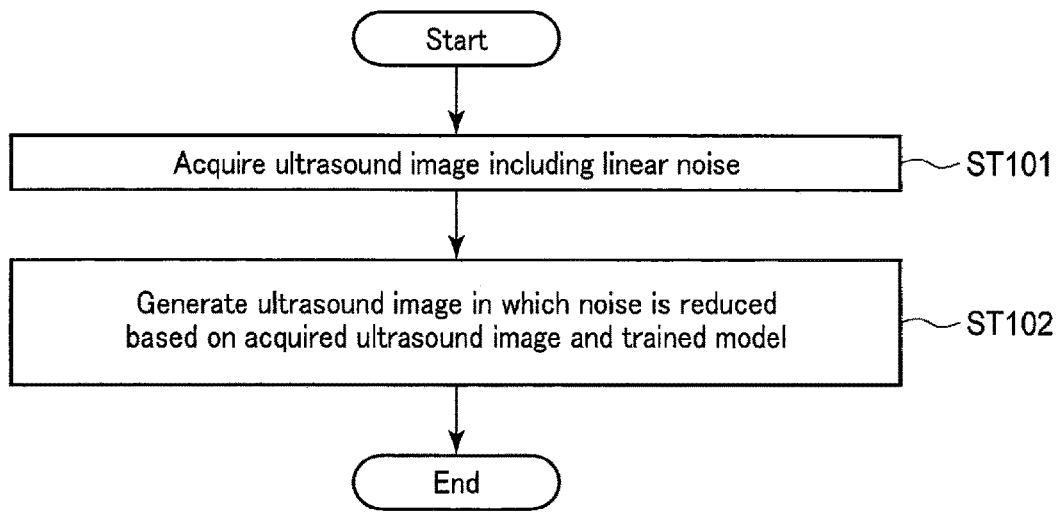
FIG. 7 is a flowchart explaining an operation of the medical image processing apparatus according to the first embodiment.

FIG. 7 is a flowchart explaining the operation of the medical image processing apparatus according to the first embodiment. The flowchart of FIG. 7 starts by the processing circuitry 11 executing a program to reduce noise (a noise reduction program), which, for example, is triggered by an instruction to activate an application relating to the noise reduction processing input by an operator operating the terminal device 2.

(Step ST101)

When the noise reduction program is executed, the processing circuitry 11 executes the acquisition function 11*a*. When the acquisition function 11*a* is executed, the processing circuitry 11 acquires an ultrasound image including linear noise that is designated by an operator from the medical image management system 3. The ultrasound image to be acquired corresponds to, for example, the ultrasound image 61 of FIG. 6.

(Step ST102)

After acquiring the ultrasound image including linear noise, the processing circuitry 11 executes the noise reduction function 11*b*. When the noise reduction function 11*b* is executed, the processing circuitry 11 generates an ultrasound image in which noise is reduced based on the acquired ultrasound image and a trained model. The generated ultrasound image corresponds to, for example, the ultrasound image 62 of FIG. 6.

The processing circuitry 11 stores the generated ultrasound image in the medical image management system 3, displays the generated ultrasound image on a display of the terminal device 2, and ends the noise reduction program.

As explained above, the medical image processing apparatus according to the first embodiment acquires an input image based on reception data collected by transmitting/receiving the ultrasound, and generates the output image by inputting the input image to the trained model for generating, based on an input image, an output image in which noise is reduced according to the wavefront shape of when the ultrasound is transmitted in an input image. Furthermore, the present medical image processing apparatus may generate the output image by a trained model according to the wavefront shape.

Alternatively, the medical image processing apparatus according to the first embodiment acquires an ultrasound image including linear noise, and generates an ultrasound image in which noise is reduced by inputting the acquired ultrasound image to a trained model that generates an ultrasound image in which noise is reduced based on the ultrasound image including linear noise.

Accordingly, the present medical image processing apparatus is capable of reducing the linear noise occurring in the acquired ultrasound image regardless of the type of probe that has acquired the ultrasound image.

The present medical image processing apparatus is capable of using an ultrasound image including noise in accordance with the wavefront shape of the transmission wave. The present medical image processing apparatus is also capable of using an ultrasound image including noise in accordance with the wavefront shape of the transmission wave, which is a plane wave, a diffusion wave, or a focusing wave.

Second Embodiment

The medical image processing apparatus according to the first embodiment performs noise reduction processing of the ultrasound image by using a trained model. On the other hand, a model learning apparatus according to a second embodiment generates a trained model that is used by, for example, a medical image processing apparatus.

Figure 8:
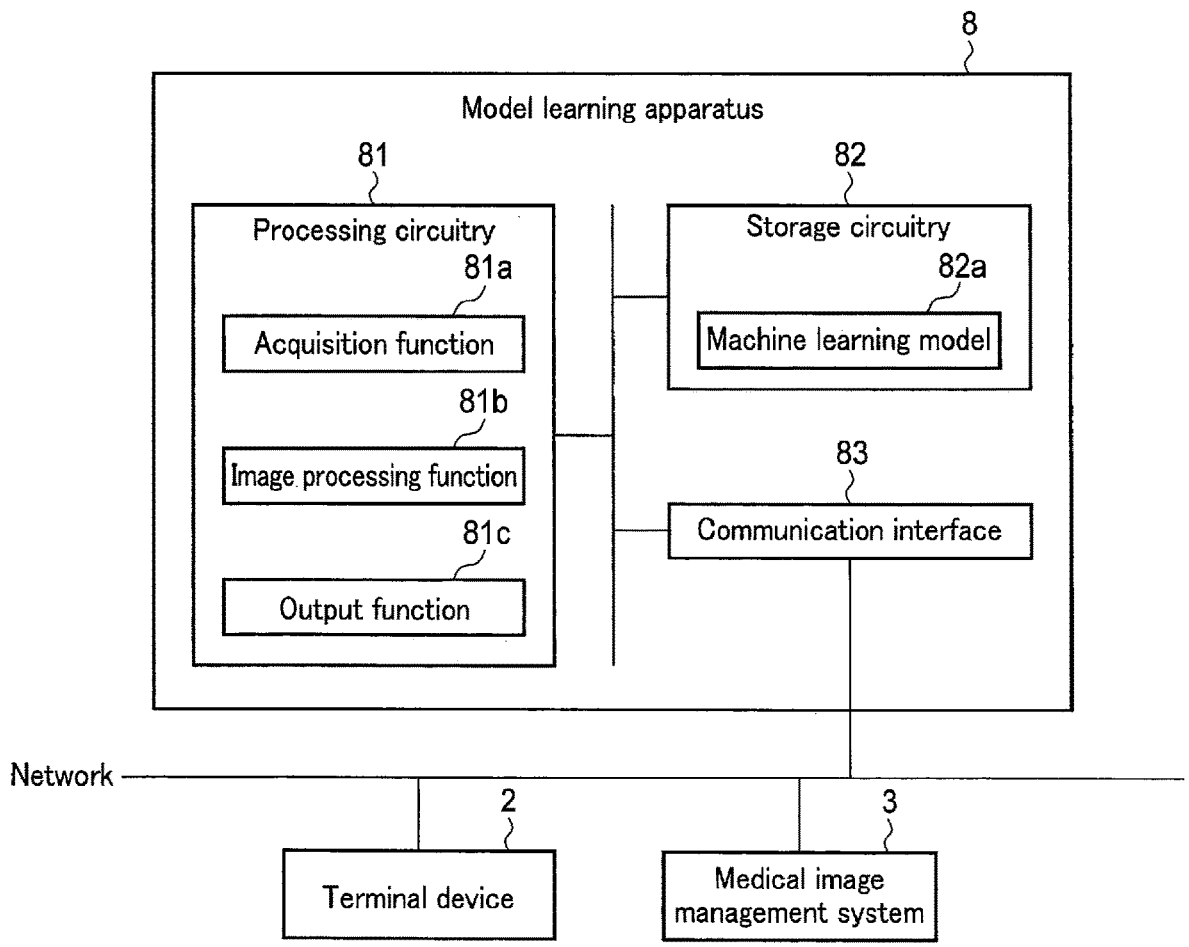
FIG. 8 is a block diagram showing a configuration example of a medical image processing system including a model learning apparatus according to a second embodiment.

FIG. 8 is a block diagram showing a configuration example of a medical image processing system including the model learning apparatus according to the second embodiment. As shown in FIG. 8, for example, the medical image processing system according to the present embodiment comprises a model learning apparatus 8, a terminal device 2, and a medical image management system 3. The model learning apparatus 8, the terminal device 2, and the medical image management system 3 are connected to each other via, for example, a network installed in a medical facility. A medical information processing system may comprise a plurality of terminal devices.

The model learning apparatus 8 comprises processing circuitry 81, storage circuitry 82, and a communication interface 83. The model learning apparatus 8 is, for example, an apparatus that generates the trained model 12*a* included in the storage circuitry 12 of the medical image processing apparatus 1 of FIG. 1.

The communication interface 83 is able to use, for example, an NIC. The communication interface 83 is, for example, a circuit relating to communications with the terminal device 2 and the medical image management system 3. In the explanations hereafter, the description will be omitted on the communication interface 83 intervening in communications between the model learning apparatus 8 and other apparatuses connected to the network.

The storage circuitry 82 stores a system control program of the model learning apparatus 8, instructions of an operator transmitted from the terminal device 2, and various data received via the network, etc. Furthermore, the storage circuitry 82 stores a machine learning model 82*a*. The storage circuitry 82 may store the machine learning model 82*a* in advance of delivery of the model learning apparatus 8. Alternatively, the storage circuitry 82 may store the machine learning model 82*a* acquired from a server device, etc. (not shown) after the model learning apparatus 8 is delivered. The storage circuitry 82 may also store mask data that is described later.

The processing circuitry 81 comprises, as hardware resources, a processor and a memory. The processing circuitry 81 reads the system control program stored in the storage circuitry 82 in accordance with the instructions input by the operator via the terminal device 2. The processing circuitry 81 executes each function relating to processing for performing machine learning of the machine learning model (model learning processing) in accordance with the read system control program. Each of the above functions is, for example, an acquisition function 81a, an image processing function 81b, and an output function 81c. The processing circuitry 81 that executes the acquisition function 81a may be referred to as an "acquisition unit".

By the acquisition function 81a, the processing circuitry 81 acquires an input image based on reception data collected by transmitting/receiving ultrasound. Specifically, by the acquisition function 81a, the processing circuitry 81 acquires, for example, an ultrasound image from the medical image management system 3. Furthermore, the processing circuitry 81 acquires, for example, mask data from the storage circuitry 82. The mask data includes, for example, position information of linear noise to be given to the ultrasound image. The mask data is, for example, an image showing only the linear noise, and the mask data shows a straight linear picture or an arcuate picture. The processing circuitry 81 may acquire a plurality of ultrasound images obtained by cutting out a dynamic picture image in units of frames.

Based on the ultrasound image and the mask data, the processing circuitry 81 generates the ultrasound image including linear noise by the image processing function 81b. Specifically, the processing circuitry 81 uses the mask data to perform processing for adding linear noise to the ultrasound image. In other words, the processing circuitry 81 adds a straight linear picture or an arcuate picture to the ultrasound image. The ultrasound image is, for example, a B mode image which expresses the intensity of the received ultrasound by luminance. Furthermore, the processed ultrasound image corresponds to, for example, an ultrasound image including linear noise, and is an image to which a picture is added to include a pixel with relatively high luminance among pixel groups that configure the ultrasound image prior to processing.

By the output function 81c, the processing circuitry 81 outputs the machine learning model 82a with the acquired ultrasound image and the processed ultrasound image as the training data. The training data is used for a machine learning model which is to be a trained model that functions to receive an ultrasound image including linear noise, and output an ultrasound image, corresponding to such ultrasound image, in which noise is reduced.

Furthermore, the processing circuitry 81 may store the machine learning model 82a in its own memory, etc. That is, instead of storing the program (the machine learning model 82a) in the storage circuitry 82, the program may be incorporated directly into circuitry of the processor. In this case, the processor reads and executes the program incorporated into the circuitry to realize the corresponding function. Furthermore, the machine learning model 82a may be implemented on the circuitry of ASIC and FPGA, etc., and such circuitry may be incorporated into the processing circuitry 81.

Figure 9:
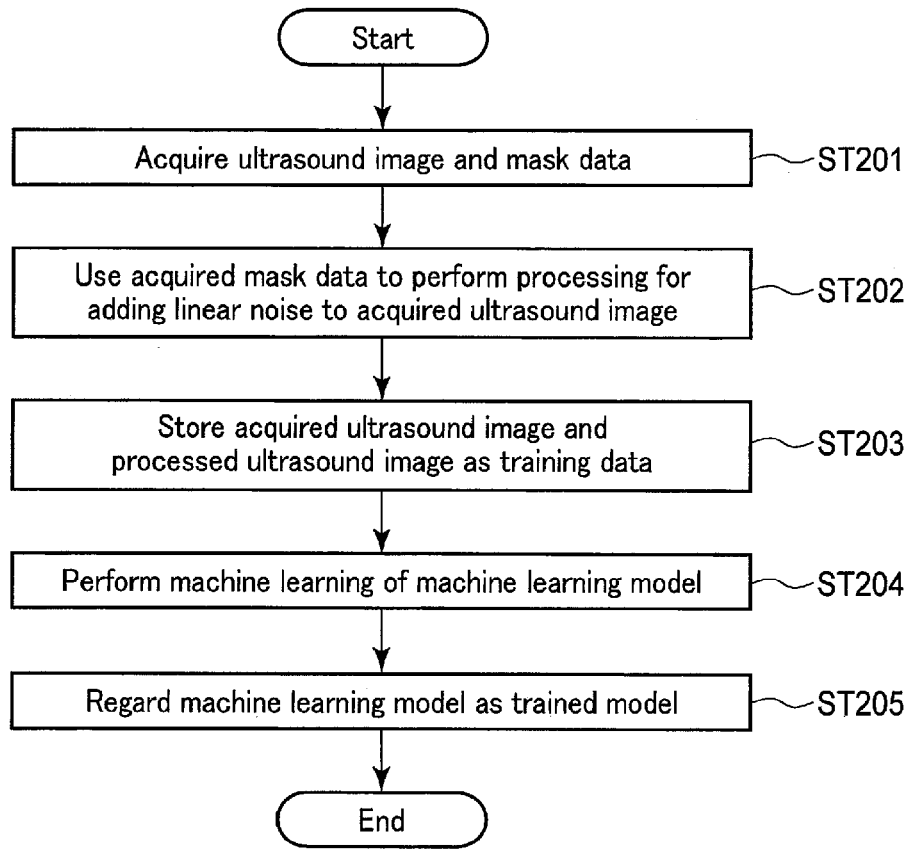
FIG. 9 is a flowchart explaining an operation of the model learning apparatus according to the second embodiment.

The operation of the model learning apparatus 8 according to the second embodiment configured in the above manner will now be explained in accordance with the processing procedure of processing circuitry 81. Hereinafter, explanations will be made by using the flowchart of FIG. 9, and the schematic view of FIG. 10. FIG. 9 is a flowchart explaining an operation of the model learning apparatus according to the second embodiment. FIG. 10 is a drawing schematically showing an operation of the model learning apparatus according to the second embodiment.

The flowchart of FIG. 9 starts by the processing circuitry 81 executing a program for performing machine learning of a machine learning model (a model learning program), which, for example, is triggered by an instruction to activate an application relating to the model learning processing input by an operator operating the terminal device 2.

(Step ST201)

When the model learning program is executed, the processing circuitry 81 executes the acquisition function 81a. When the acquisition function 81a is executed, the processing circuitry 81 acquires an ultrasound image that is designated by the operator from the medical image management system 3. The ultrasound image to be acquired corresponds to, for example, an ultrasound image 101 of FIG. 10.

The processing circuitry 81 also acquires mask data designated by the operator from the storage circuitry 82. The mask data to be acquired corresponds to, for example, mask data 102 of FIG. 10.

(Step ST202)

After acquiring the ultrasound image and the mask data, the processing circuitry 81 executes the image processing function 81b. When the image processing function 81b is executed, the processing circuitry 81 uses the acquired mask data to perform processing for adding linear noise to the acquired ultrasound image.

For example, the processing circuitry 81 generates an ultrasound image 103 including linear noise by using the mask data 102 to perform processing for adding linear noise to the ultrasound image 101.

(Step ST203)

After generating the ultrasound image including linear noise, the processing circuitry. 81 stores the acquired ultrasound image and the generated ultrasound image in the storage circuitry 82 as the training data.

(Step ST204)

After storing the training data, the processing circuitry 81 outputs the training data stored in the storage circuitry 82 sequentially to the machine learning model 82a by the output function 81c. The processing circuitry 81 uses the training data to perform machine learning of the machine learning model 82a, and adjusts parameters of the machine learning model 82a.

For example, the processing circuitry 81 performs machine learning of the machine learning model 82a by using the ultrasound image 103 including linear noise and the ultrasound image 101 as the training data.

(Step ST205)

After performing the machine learning of the machine learning model 82a, the processing circuitry 81 regards the machine learning model 82a as a trained model and ends the model learning program.

In other words, the trained model in step ST205 corresponds to a model that is trained by using a first image, which is the ultrasound image, and a second image in which a straight linear picture or an arcuate picture is added to the first image. The first image may be a B mode image expressing the intensity of the received ultrasound by luminance, and the second image may be an image in which a picture is added to include a pixel with relatively high luminance among pixel groups configuring the first image.

As explained above, the model learning apparatus according to the second embodiment acquires the ultrasound image and the mask data as a training data producing apparatus, and uses the acquired mask data to perform processing for adding linear noise to the acquired ultrasound image. The model learning apparatus outputs the acquired ultrasound image and the processed ultrasound image as the training data to be used for the machine learning model.

Therefore, as the training data producing apparatus, the present model learning apparatus is capable of producing the training data to be used for the trained model, which is for reducing noise in accordance with the wavefront shape of the transmission wave occurring in the ultrasound image.

Third Embodiment

The medical image processing apparatus according to the first embodiment performs noise reduction processing of the ultrasound image by using one trained model. On the other hand, a medical image processing apparatus according to a third embodiment performs noise reduction processing of an ultrasound image by using one of a plurality of trained models.

Figure 11:
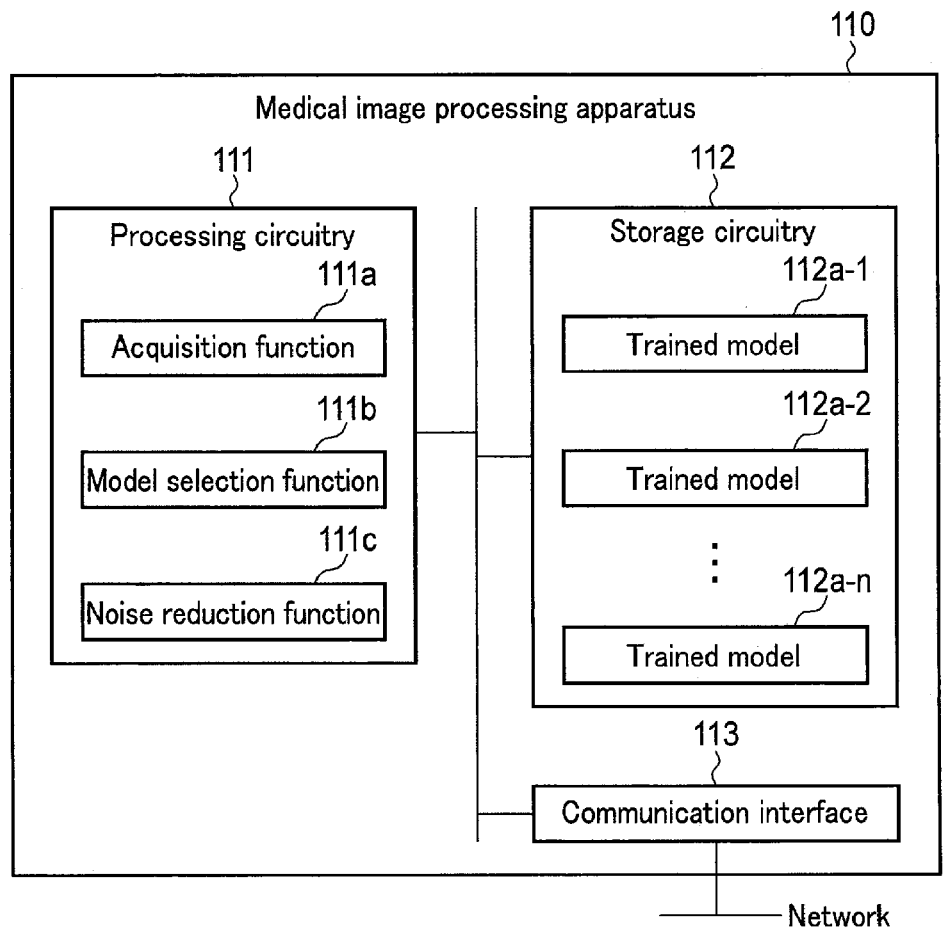
FIG. 11 is a block diagram showing a configuration example of a medical image processing apparatus according to a third embodiment.

FIG. 11 is a block diagram showing a configuration example of the medical image processing apparatus according to the third embodiment. For example, as shown in FIG. 11, a medical image processing apparatus 110 comprises processing circuitry 111, storage circuitry 112, and a communication interface 113. The medical image processing apparatus 110 is an apparatus that generates an ultrasound image in which noise is reduced by applying, for example, processing using machine learning with respect to an ultrasound image including noise in accordance with a wavefront shape of a transmission wave.

The medical image processing apparatus 110 may be connected to a terminal device and a medical image management system via a network. Since the terminal device and the medical image management system are the same as the terminal device 2 and the medical image management system 3 of FIG. 1, the drawing and explanation thereof will be omitted. The same applies to each of the following embodiments.

The communication interface 113 is able to use, for example, an NIC. The communication interface 113 is, for example, a circuit relating to communications with the terminal device and the medical image management system. In the explanations hereafter, the description will be omitted on the communication interface 113 intervening in communications between the medical image processing apparatus 110 and other apparatuses connected to the network.

The storage circuitry 112 stores a system control program of the medical image processing apparatus 110, instructions of an operator transmitted from the terminal device, and various data received via the network, etc. Furthermore, the storage circuitry 112 stores a plurality of trained models 112a-1, 112a-2, ..., and 112a-n (n is a positive integer). Hereinafter, explanations will be made by referring to the plurality of trained models 112a-1, 112a-2, ..., and 112a-n collectively as a plurality of trained models 112A. Furthermore, explanations on matters in common to each of the trained models of the plurality of trained models 112A will be made by referring to such models as a trained model 112a. The storage circuitry 112 may store the plurality of trained models 112A in advance of delivery of the medical image processing apparatus 110. Alternatively, the storage circuitry 112 may store the trained models 112A acquired from a server device, etc. (not shown) after the medical image processing apparatus 110 is delivered.

The trained model 112a is a trained machine learning model that is obtained by performing machine learning on a machine learning model in accordance with a model learning program based on the training data. Here, the trained model 112a of the present embodiment is provided with a function to output an ultrasound image in which noise is reduced based on an input of an ultrasound image that includes linear noise. In this case, the training data includes input data, which is an ultrasound image including linear noise, and output data, which is an ultrasound image in which the noise is reduced.

Each of the trained models of the plurality of trained models 112A has a different type of ultrasound image of the processing target. For example, the trained model 112a-1 is produced relating to an ultrasound image that is generated by using a convex probe, and noise that is similar to a wavefront shape of a plane wave in the convex probe. Furthermore, each of the trained model of the plurality of trained models 112A corresponds to information relating to the wavefront shape of the transmission wave. The information relating to the wavefront shape of the transmission wave includes, for example, probe information and transmission profile information described later.

The processing circuitry 111 comprises, as hardware resources, a processor and a memory. The processing circuitry 111 reads a system control program stored in the storage circuitry 112 in accordance with an instruction input by an operator via the terminal device. The processing circuitry 111 executes each function relating to the noise reduction processing in accordance with the read system control program. Each of the above functions is, for example, an acquisition function 111a, a model selection function 111b, and a noise reduction function 111c. The processing circuitry ill that executes the acquisition function 111a may be referred to as an "acquisition unit", and the processing circuitry 111 that executes the model selection function 111b and the noise reduction function 111c may be referred to as a "processing unit".

By the acquisition function 111a, the processing circuitry 111 acquires an input image based on reception data collected by transmitting/receiving ultrasound. Furthermore, by an acquisition function 141a, processing circuitry 141 acquires supplementary information indicating at least one of probe information (the type of ultrasound probe) or a delay profile described later relating to the reception data or the input image.

Specifically, by the acquisition function 111a, the processing circuitry 111 acquires, for example, an ultrasound image including linear noise from the medical image management system. Furthermore, the processing circuitry 111 acquires the probe information and the transmission profile information that correspond to the acquired ultrasound image.

The probe information and the transmission profile information are examples of information relating to the wavefront shape of the transmission wave described above, and are used for identifying the wavefront shape of the transmission wave. The probe information includes, for example, information relating to the type of ultrasound probe used for acquiring the ultrasound image. The type of ultrasound probe corresponds to, for example, the types of probe including a sector probe, a linear probe, and a convex probe. Furthermore, even among the same convex probe, the type of ultrasound probe may differ in accordance with the structure of the probe, such as the curvature of the arrangement surface of an oscillator, etc. The transmission profile information includes, for example, information relating to the setting of a delay amount (a delay profile) to be applied when each oscillator is driven. The transmission profile information may include, for example, information of other than the delay profile, such as information relating to the setting of an opening to be used for wave transmission.

By the model selection function 111b, the processing circuitry 111 determines the trained model based on the supplementary information indicating at least one of the type of ultrasound probe or the delay profile attached to the reception data or the input image. In other words, by the model selection function 111b, the processing circuitry 111 selects, from the plurality of trained models 112A, a trained model according to at least one of the acquired probe information (a type of probe) or the transmission profile information.

Furthermore, the correspondence between a combination of the probe information and the transmission profile information and the trained model is not limited to one-to-one, and may also be many-to-one. For example, a combination of probe information A and transmission profile information A, and a combination of the probe information A and transmission profile information B may each correspond to the same trained model A. Furthermore, for example, the combination of the probe information A and the transmission profile information A, and a combination of probe information B and the transmission profile information B may each correspond to the same trained model.

By the noise reduction function 111c, the processing circuitry 111 generates an output image by inputting the input image to a trained model for generating, based on an input image, an output image in which noise is reduced according to the wavefront shape of when the ultrasound is transmitted in an input image. Furthermore, since the trained model selected by the model selection function 111b is used, the processing circuitry 111 may also generate the output image by inputting the input image to the trained model according to at least one of the type of ultrasound probe or the delay profile.

Specifically, by the noise reduction function 111c, the processing circuitry 111 generates an ultrasound image in which noise is reduced by inputting an ultrasound image including linear noise to a trained model that generates an ultrasound image in which noise is reduced based on the ultrasound image including linear noise. In other words, the processing circuitry 111 generates the ultrasound image in which noise is reduced by inputting the ultrasound image including linear noise to the selected trained model.

Furthermore, the processing circuitry 111 may store the plurality of trained models 112A in its own memory, etc. That is, instead of storing a program in the storage circuitry 112 (the plurality of trained models 112A), the program may be incorporated directly into the processor. In this case, the processor reads and executes the program incorporated into the circuitry to realize the corresponding function. Furthermore, the plurality of trained models 112A may be implemented on the circuitry of ASIC and FPGA, etc., and such circuitry may be incorporated into the processing circuitry 111.

Figure 12:
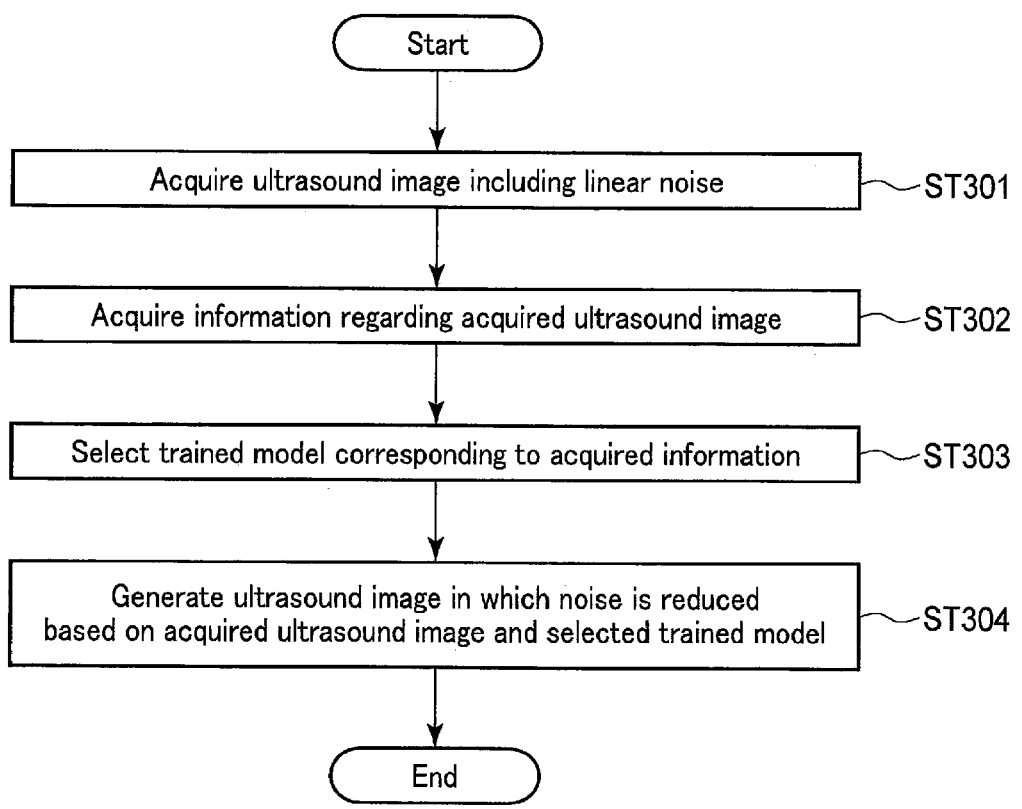
FIG. 12 is a flowchart explaining an operation of the medical image processing apparatus according to the third embodiment.

The operation of the medical image processing apparatus 110 according to the third embodiment configured in the above manner will now be explained in accordance with the processing procedure of processing circuitry 111. Hereinafter, explanations will be made by using the flowchart of FIG. 12, and the schematic view of FIG. 13. FIG. 12 is a flowchart explaining an operation of the medical image processing apparatus according to the third embodiment. FIG. 13 is a drawing schematically showing the operation of the medical image processing apparatus according to the third embodiment.

The flowchart of FIG. 12 starts by the processing circuitry 111 executing a noise reduction program, which, for example, is triggered by an instruction to activate an application relating to the noise reduction processing input by an operator operating the terminal device.

(Step ST301)

When the noise reduction program is executed, the processing circuitry 111 executes the acquisition function 111a. When the acquisition function 111a is executed, the processing circuitry 111 acquires an ultrasound image including linear noise that is designated by the operator from the medical image management system. The ultrasound image to be acquired corresponds to, for example, an ultrasound image 131 of FIG. 13. The ultrasound image 131 has arc noise 131b in a drawing region 131a.

(Step ST302)

The processing circuitry 111 then acquires information on the acquired ultrasound image by the acquisition function 111a. Specifically, the processing circuitry 111 acquires probe information and transmission profile information relating to the acquired ultrasound image. For example, probe information 132 and transmission profile information 133 are attached to the ultrasound image 131 of FIG. 13.

(Step ST303)

After acquiring the ultrasound image, the probe information, and the transmission profile information, the processing circuitry 111 executes the model selection function 111b. When the model selection function 111b is executed, the processing circuitry 111 selects a trained model corresponding to the acquired information from a plurality of trained models. Specifically, the processing circuitry 111 selects a trained model according to at least one of the acquired probe information or the transmission profile information from the plurality of trained models.

For example, from the plurality of trained models 112A, the processing circuitry 111 selects a trained model 112a-2 corresponding to the probe information 132 and the transmission profile information 133.

(Step ST304)

After selecting the trained model, the processing circuitry 111 executes the noise reduction function 111c. When the noise reduction function 111c is executed, the processing circuitry 111 generates an ultrasound image in which noise is reduced based on the acquired ultrasound image and the selected trained model. The ultrasound image to be generated corresponds to, for example, an ultrasound image 134 of FIG. 13. The ultrasound image 134 is obtained by reducing the arc noise 131b in the ultrasound image 131.

For example, the processing circuitry 111 generates the ultrasound image 134 based on the ultrasound image 131 and the trained model 112a-2.

The processing circuitry 111 stores the generated ultrasound image in the medical image management system, displays the generated ultrasound image on a display of the terminal device, and ends the noise reduction program.

As explained above, the medical image processing apparatus according to the third embodiment acquires an input image based on the reception data collected by transmitting/receiving the ultrasound, and generates an output image by inputting the input image to a trained model for generating, based on the input image, an output image in which noise is reduced according to the wavefront shape of when the ultrasound is transmitted in an input image.

Furthermore, the reception data may be collected by using an ultrasound probe including a plurality of vibration elements driven in accordance with the delay profile, and the present medical image processing apparatus may generate the output image by a trained model according to at least one of the type of ultrasound probe or the delay profile.

Furthermore, the present medical image processing apparatus may determine the trained model based on supplementary information indicating at least one of the type of ultrasound probe or the delay profile attached to the reception data or the input image.

Furthermore, the trained model may be a model that is trained by using a first image, which is the ultrasound image, and a second image, which is obtained by adding a straight linear picture or an arcuate picture to the first image. The first image may be a B mode image expressing the intensity of the received ultrasound by luminance, and the second image may be an image in which the picture is added to include a pixel with relatively high luminance among pixel groups configuring the first image.

Alternatively, the medical image processing apparatus according to the third embodiment acquires an ultrasound image including linear noise and information on the ultrasound image, and selects the trained model corresponding to the acquired information from a plurality of trained models. The medical image processing apparatus generates an ultrasound image in which noise is reduced by inputting the acquired ultrasound image to the selected trained model that generates an ultrasound image in which noise is reduced based on the ultrasound image including linear noise.

Alternatively, the medical image processing apparatus according to the third embodiment acquires an input image based on reception data collected by transmitting/receiving ultrasound by using an ultrasound probe including a plurality of vibration elements driven in accordance with a delay profile, and stores a plurality of trained models for generating, based on an input image, an output image in which noise is reduced according to the wavefront shape of when the ultrasound is transmitted in an input image. A trained model corresponding to the type of ultrasound probe or the delay profile is selected from the plurality of trained models, and the input image is input to the selected trained model to generate an output image.

Accordingly, the present medical image processing apparatus is capable of performing noise reduction processing by using a trained model that is suitable for the probe acquiring the ultrasound image.

Furthermore, the present medical image processing apparatus is capable of using the probe information and the transmission profile information as the acquired information. The present medical image processing apparatus is also capable of using an ultrasound image including noise in accordance with the wavefront shape of the transmission wave. The present medical image processing apparatus is also capable of using an ultrasound image including noise in accordance with the wavefront shape of the transmission wave, which is a plane wave, a diffusion wave, or a focusing wave.

Fourth Embodiment

The medical image processing apparatus according to the first embodiment performs noise reduction processing of the ultrasound image by using a trained model corresponding to both the straight noise and the arc noise. On the other hand, a medical image processing apparatus according to a fourth embodiment, for example, performs noise reduction processing of an ultrasound image including arc noise even if a trained model corresponds only to straight noise. In the present embodiment, although a trained model corresponding only to the straight noise is explained, the embodiment is not limited thereto.

FIG. 14 is a block diagram showing a configuration example of the medical image processing apparatus according to the fourth embodiment. For example, as shown in FIG. 14, a medical image processing apparatus 140 comprises processing circuitry 141, storage circuitry 142, and a communication interface 143. The medical image processing apparatus 140 is an apparatus that generates an ultrasound image in which noise is reduced by applying, for example, processing using machine learning with respect to an ultrasound image including noise in accordance with a wavefront shape of a transmission wave.

The communication interface 143 is able to use, for example, an NIC. The communication interface 143 is, for example, a circuit relating to communications with a terminal device and a medical image management system. In the explanations hereafter, the description will be omitted on the communication interface 143 intervening in communications between the medical image processing apparatus 140 and other apparatuses connected to the network.

The storage circuitry 142 stores a system control program of the medical image processing apparatus 140, instructions of an operator transmitted from the terminal device, and various data received via the network, etc. Furthermore, the storage circuitry 142 stores a trained model 142a. The storage circuitry 142 may store the trained model 142a in advance of delivery of the medical image processing apparatus 140. Alternatively, the storage circuitry 142 may store the trained model 142a acquired from a server device, etc. (not shown) after the medical image processing apparatus 140 is delivered.

The trained model 142a is a trained machine learning model that is obtained by performing machine learning on a machine learning model in accordance with a model learning program based on training data. Here, for example, the trained model 112a of the present embodiment is provided with a function to output an ultrasound image in which noise is reduced based on an input of an ultrasound image that includes straight noise. In this case, the training data includes input data, which is an ultrasound image including straight noise, and output data, which is an ultrasound image in which the noise is reduced.

The processing circuitry 141 comprises, as hardware resources, a processor and a memory. The processing circuitry 141 reads a system control program stored in the storage circuitry 142 in accordance with an instruction input by the operator via the terminal device. The processing circuitry 141 executes each function relating to the noise reduction processing in accordance with the read system control program. Each of the above functions is, for example, an acquisition function 141a, a wavefront determination function 141b, an image correction function 141c, a noise reduction function 141d, and an image reverse correction function 141e. The processing circuitry 141 that executes the acquisition function 141a may be referred to as an "acquisition unit", and the processing circuitry 141 that executes the noise reduction function 141d may be referred to as a "processing unit".

By the acquisition function 141a, the processing circuitry 141 acquires an input image based on reception data collected by transmitting/receiving ultrasound. Furthermore, by the acquisition function 141a, the processing circuitry 141 acquires supplementary information indicating at least one of the type of ultrasound probe or a delay profile attached to the reception data or the input image.

Specifically, by the acquisition function 141a, the processing circuitry 141 acquires, for example, an ultrasound image including linear noise from the medical image management system. Furthermore, the processing circuitry 141 acquires probe information and transmission profile information that correspond to the acquired ultrasound image.

By the wavefront determination function 141b, the processing circuitry 141 determines a wavefront that may be included in the acquired ultrasound image. Here, the wavefront expresses the shape of a transmission wave, and corresponds to a noise shape. Specifically, the processing circuitry 141 determines the noise shape that may be included in the ultrasound image based on the acquired probe information and transmission profile information.

In the case where the noise shape is straight (that is, straight noise), the processing circuitry 141 omits the processing of the image correction function 141c and the image reverse correction function 141e described later, and performs only the noise reduction function 141d processing with respect to the acquired ultrasound image. In the case where the noise shape is arcuate (that is, arc noise), the processing circuitry 141 performs the image correction function 141c, the noise reduction function 141d, and the image reverse correction function 141e.

By the image correction function 141c, the processing circuitry 141 corrects the ultrasound image including the arc noise so that the arc noise is regarded as the straight noise. Specifically, the processing circuitry 141 calculates a curvature of the arc based on the acquired probe information and transmission profile information, and corrects the acquired ultrasound image based on the calculated curvature. For the correction, for example, distortion correction, etc. is used with respect to a curved surface.

By the noise reduction function 141d, the processing circuitry 141 generates an output image by inputting the input image to a trained model for generating, based on an input image, an output image in which noise is reduced according to the wavefront shape of when the ultrasound is transmitted in an input image. Specifically, by the noise reduction function 141d, the processing circuitry 141 generates an ultrasound image in which noise is reduced by inputting an ultrasound image including straight noise to a trained model that generates an ultrasound image in which noise is reduced based on an ultrasound image including straight noise. In other words, the processing circuitry 141 generates an ultrasound image in which noise is reduced by inputting an ultrasound image including straight noise to a trained model. The ultrasound image to be processed by the noise reduction function 141d is, for example, the ultrasound image including straight noise that is acquired by the acquisition function 141a and the ultrasound image that is corrected by the image correction function 141c.

By the image reverse correction function 141e, the processing circuitry 141 performs reverse correction, which is a reversed correction of the correction executed by the image correction function 141c, with respect to the ultrasound image in which noise is reduced, which corresponds to the ultrasound image corrected by the image correction function 141c.

The processing circuitry 141 may store the trained model 142a in its own memory, etc. That is, instead of storing a program (the trained model 142a) in the storage circuitry 142, the program may be incorporated directly into circuitry of the processor. In this case, the processor reads and executes the program incorporated into the circuitry to realize the corresponding function. Furthermore, the trained model 142a may be implemented on the circuitry of ASIC and FPGA, etc., and such circuitry may be incorporated into the processing circuitry 141.

The operation of the medical image processing apparatus 140 according to the fourth embodiment configured in the above manner will now be explained in accordance with the processing procedure of processing circuitry 141. Hereinafter, explanations will be made by using the flowchart of FIG. 15, and the schematic view of FIG. 16. FIG. 15 is a flowchart explaining the operation of the medical image processing apparatus according to the fourth embodiment. FIG. 16 is a drawing schematically showing the operation of the medical image processing apparatus according to the fourth embodiment.

The flowchart of FIG. 15 starts by the processing circuitry 141 executing the noise reduction program, which, for example, is triggered by an instruction to activate an application relating to the noise reduction processing input by the operator operating the terminal device.

(Step ST401)

When the noise reduction program is executed, the processing circuitry 141 executes the acquisition function 141a. When the acquisition function 141a is executed, the processing circuitry 141 acquires an ultrasound image including linear noise that is designated by the operator from the medical image management system. The ultrasound image to be acquired corresponds to, for example, an ultrasound image 161 of FIG. 16. The ultrasound image 161 has arc noise 161b in a drawing region 161a.

(Step ST402)

The processing circuitry 141 then acquires information on the acquired ultrasound image by the acquisition function 141a. Specifically, the processing circuitry 141 acquires probe information and transmission profile information relating to the acquired ultrasound image. For example, probe information 162 and transmission profile information 163 are attached to the ultrasound image 161 of FIG. 16.

(Step ST403)

After acquiring the ultrasound image, the probe information, and the transmission profile information, the processing circuitry 141 executes the wavefront determination function 141b. When the wavefront determination function 141b is executed, the processing circuitry 141 determines a wavefront corresponding to the acquired information. Specifically, the processing circuitry 141 determines the noise shape included in the ultrasound image based on the acquired probe information and transmission profile information.

For example, the processing circuitry 141 determines the noise shape included in the ultrasound image 161 based on the probe information 162 and transmission profile information 163.

(Step ST404)

In the case where the determined noise is not straight noise (that is, arc noise), the processing circuitry 141 performs the processing of the image correction function 141c and the processing of the image reverse correction function 141e with respect to the ultrasound image relating to the determination. Here, the processing proceeds to step ST405.

On the other hand, in the case where the determined noise is the straight noise, the processing circuitry 141 does not perform the processing of the image correction function 141c and the processing of the image reverse correction function 141e with respect to the ultrasound image relating to the determination. Here, the processing proceeds to step ST408.

(Step ST405)

After the noise shape is determined, the processing circuitry 141 executes the image correction function 141c. When the image correction function 141c is executed, the processing circuitry 141 corrects the ultrasound image including the arc noise so that the arc noise is regarded as the straight noise. The corrected ultrasound image corresponds to, for example, an ultrasound image 164 of FIG. 16.

For example, the processing circuitry 141 generates the ultrasound image 164 by correcting the ultrasound image 161 including the arc noise 161b. The ultrasound image 164 includes pseudo straight noise 164b which is obtained by distorting the arc noise 161b in a drawing region 164a.

(Step ST406)

After correcting the ultrasound image, the processing circuitry 141 executes the noise reduction function 141d. When the noise reduction function 141d is executed, the processing circuitry 141 generates the ultrasound image in which the noise is reduced based on the corrected ultrasound image and the trained model. The ultrasound image to be generated corresponds to, for example, an ultrasound image 165 of FIG. 16. The ultrasound image 165 is obtained by reducing the pseudo straight noise 164b in the ultrasound image 164.

For example, the processing circuitry 141 generates the ultrasound image 165 based on the ultrasound image 164 and the trained model 142a.

(Step ST407)

After generating the ultrasound image in which noise is reduced, the processing circuitry 141 executes the image reverse correction function 141e. When the image reverse correction function 141e is executed, the processing circuitry 141 performs reverse correction, which is a reversed correction of the correction executed by the image correction function 141c, with respect to the ultrasound image in which noise is reduced, which corresponds to the ultrasound image corrected by the image correction function 141c. The ultrasound image to which the reverse correction has been applied corresponds to, for example, an ultrasound image 166 of FIG. 16. The ultrasound image 166 is obtained by reducing the arc noise 161b in the ultrasound image 161.

For example, the processing circuitry 141 generates the ultrasound image 166 by performing reverse correction, which is a reversed correction of the correction executed by the image correction function 141c, with respect to the ultrasound image 165.

After step ST407, the processing circuitry 141 stores the generated ultrasound image in the medical image management system, displays the generated ultrasound image on a display of the terminal device, and ends the noise reduction program.

(Step ST408)

After the noise shape is determined, the processing circuitry 141 executes the noise reduction function 141d. When the noise reduction function 141d is executed, the processing circuitry 141 generates the ultrasound image in which noise is reduced based on the acquired ultrasound image and the trained model. The ultrasound image to be processed in step ST408 is the ultrasound image including straight noise that is acquired by the acquisition function 141a.

After step ST408, the processing circuitry 141 stores the generated ultrasound image in the medical image management system, displays the generated ultrasound image on a display of the terminal device, and ends the noise reduction program.

As explained above, the medical image processing apparatus according to the fourth embodiment acquires an ultrasound image including linear noise and information relating to the ultrasound image, and determines a wavefront corresponding to the acquired information. In the case where the wavefront is arcuate, the medical image processing apparatus corrects the acquired ultrasound image in a manner that the arcuate noise is regarded as straight linear noise. The medical image processing apparatus inputs the corrected ultrasound image to the trained model that generates an ultrasound image in which noise is reduced based on the corrected ultrasound image, and, thereby, generates an ultrasound image in which the noise is reduced in the corrected ultrasound image, and performs reverse correction on the generated ultrasound image.

Accordingly, even with a trained model trained by limited noise shapes, the present medical image processing apparatus is capable of reducing the noise of other shapes occurring in the ultrasound image.

Furthermore, the present medical image processing apparatus is capable of using the probe information and the transmission profile information as the acquired information. The present medical image processing apparatus is also capable of using an ultrasound image including noise in accordance with the wavefront shape of the transmission wave. The present medical image processing apparatus is capable of using an ultrasound image including noise in accordance with the wavefront shape of the transmission wave, which is a plane wave, a diffusion wave, or a focusing wave.

Fifth Embodiment

The medical image processing apparatus according to the first embodiment performs noise reduction processing of the ultrasound image by using only a trained model. On the other hand, a medical image processing apparatus according to a fifth embodiment performs processing to determine whether or not a portion other than noise is reduced in noise reduction processing using a trained model.

Figure 17:
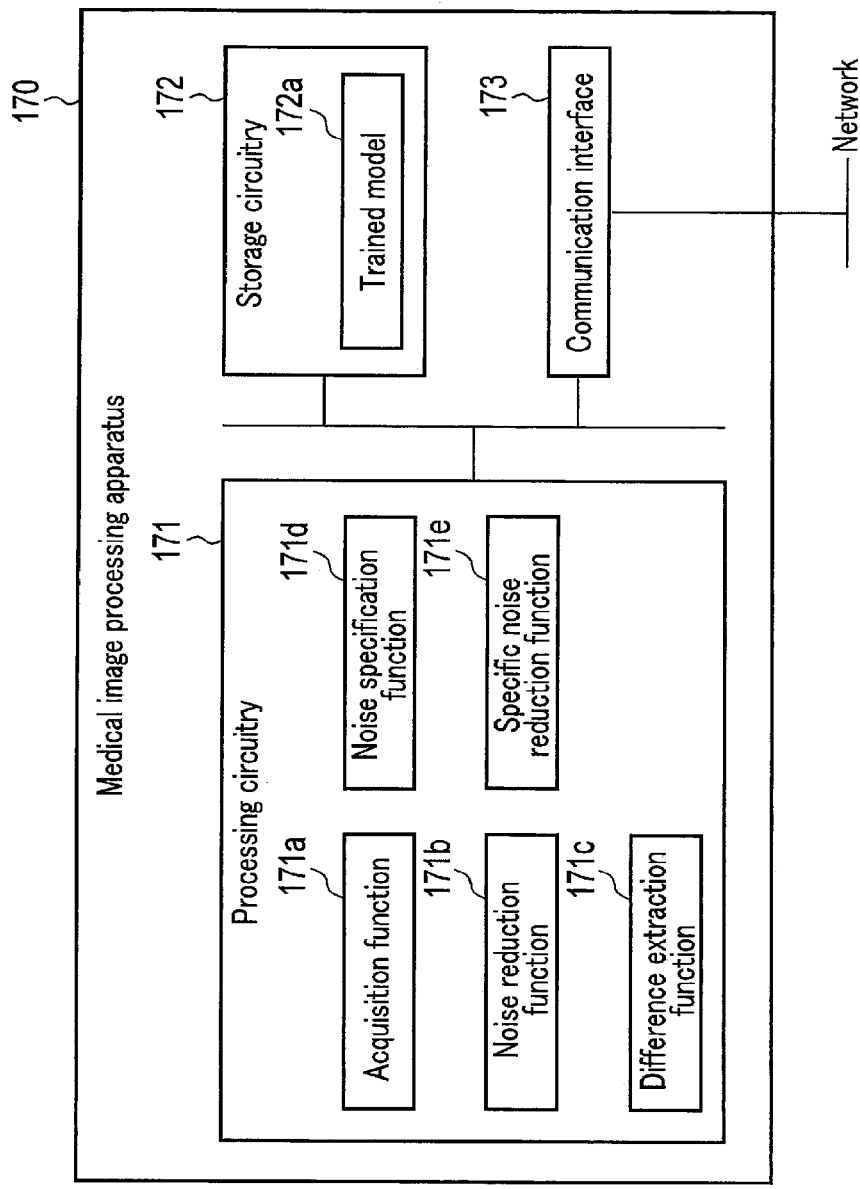
FIG. 17 is a block diagram showing a configuration example of a medical image processing apparatus according to a fifth embodiment.

FIG. 17 is a block diagram showing a configuration example of the medical image processing apparatus according to the fifth embodiment. For example, as shown in FIG. 17, a medical image processing apparatus 170 comprises processing circuitry 171, storage circuitry 172, and a communication interface 173. The medical image processing apparatus 170 is an apparatus that generates an ultrasound image in which noise is reduced by applying, for example, processing using machine learning with respect to an ultrasound image including noise in accordance with a wavefront shape of a transmission wave.

The communication interface 173 is able to use, for example, an NIC. The communication interface 173 is, for example, a circuit relating to communications with a terminal device and a medical image management system. In the explanations hereafter, the description will be omitted on the communication interface 173 intervening in communications between the medical image processing apparatus 170 and other apparatuses connected to the network.

The storage circuitry 172 stores a system control program of the medical image processing apparatus 170, instructions of an operator transmitted from the terminal device, and various data received via the network, etc. Furthermore, the storage circuitry 172 stores a trained model 172a. The storage circuitry 172 may store the trained model 172a in advance of delivery of the medical image processing apparatus 170. Alternatively, the storage circuitry 172 may store the trained model 172a acquired from a server device, etc. (not shown) after the medical image processing apparatus 170 is delivered. Since the trained model 172a is similar to the trained model 12a of FIG. 1, explanations thereof will be omitted.

The processing circuitry 171 comprises, as hardware resources, a processor and a memory. The processing circuitry 171 reads the system control program stored in the storage circuitry 172 in accordance with an instruction input by the operator via the terminal device. The processing circuitry 171 executes each function relating to the noise reduction processing in accordance with the read system control program. Each of the above functions is, for example, an acquisition function 171a, a noise reduction function 171b, a difference extraction function 171c, a noise specification function 171d, and a specified noise reduction function 171e. The processing circuitry 171 that executes the acquisition function 171a may be referred to as an "acquisition unit", and the processing circuitry 171 that executes the noise reduction function 171b may be referred to as a "processing unit".

By the acquisition function 171a, the processing circuitry 171 acquires an input image based on reception data collected by transmitting/receiving ultrasound. Specifically, by the acquisition function 171a, the processing circuitry 171 acquires, for example, an ultrasound image including linear noise from the medical image management system. Furthermore, the processing circuitry 171 acquires probe information and transmission profile information that correspond to the acquired ultrasound image.

By the noise reduction function 171b, the processing circuitry 171 generates an output image by inputting the input image to a trained model for generating, based on an input image, an output image in which noise is reduced according to the wavefront shape of when the ultrasound is transmitted in an input image. Specifically, by the noise reduction function 171b, the processing circuitry 171 generates an ultrasound image in which noise is reduced by inputting the ultrasound image including linear noise to the trained model that generates the ultrasound image in which noise is reduced based on the ultrasound image including linear noise. In other words, the processing circuitry 171 generates the ultrasound image in which noise is reduced by inputting the ultrasound image including linear noise to the trained model.

By the difference extraction function 171c, based on the acquired ultrasound image and the generated ultrasound image, the processing circuitry 171 generates a difference image from which the reduced noise is extracted. Specifically, by extracting the difference between the acquired ultrasound image and the generated ultrasound image, the processing circuitry 171 generates the difference image from which the reduced noise is extracted.

By the noise specification function 171d, the processing circuitry 171 specifies the noise included in the difference image based on the acquired probe information and transmission profile information. Specifically, the processing circuitry 171 calculates a curvature of an arc based on the acquired probe information and transmission profile information, determines that there is noise in the case where an arcuate line included in the difference image matches the calculated curvature, and determines that there is no noise in the case where the arcuate line included in the difference image does not match the calculated curvature. The processing circuitry 171 may also generate a noise specified image including specified noise.

By the specified noise reduction function 171e, the processing circuitry 171 reduces the specified noise with respect to the acquired ultrasound image, and generates an ultrasound image in which the noise is reduced. For example, by reducing a noise portion specified by the noise specification image from the acquired ultrasound image by filter processing, the processing circuitry 171 generates an ultrasound image in which the noise is reduced.

The processing circuitry 171 may store the trained model 172a in its own memory, etc. That is, instead of storing a program (the trained model 172a) in the storage circuitry 172, the program may be incorporated directly into circuitry of the processor. In this case, the processor reads and executes the program integrated into the circuitry to realize the corresponding function. Furthermore, the trained model 172a may be implemented on the circuitry of ASIC and FPGA, etc., and such circuitry may be incorporated into the processing circuitry 171.

Figure 18:
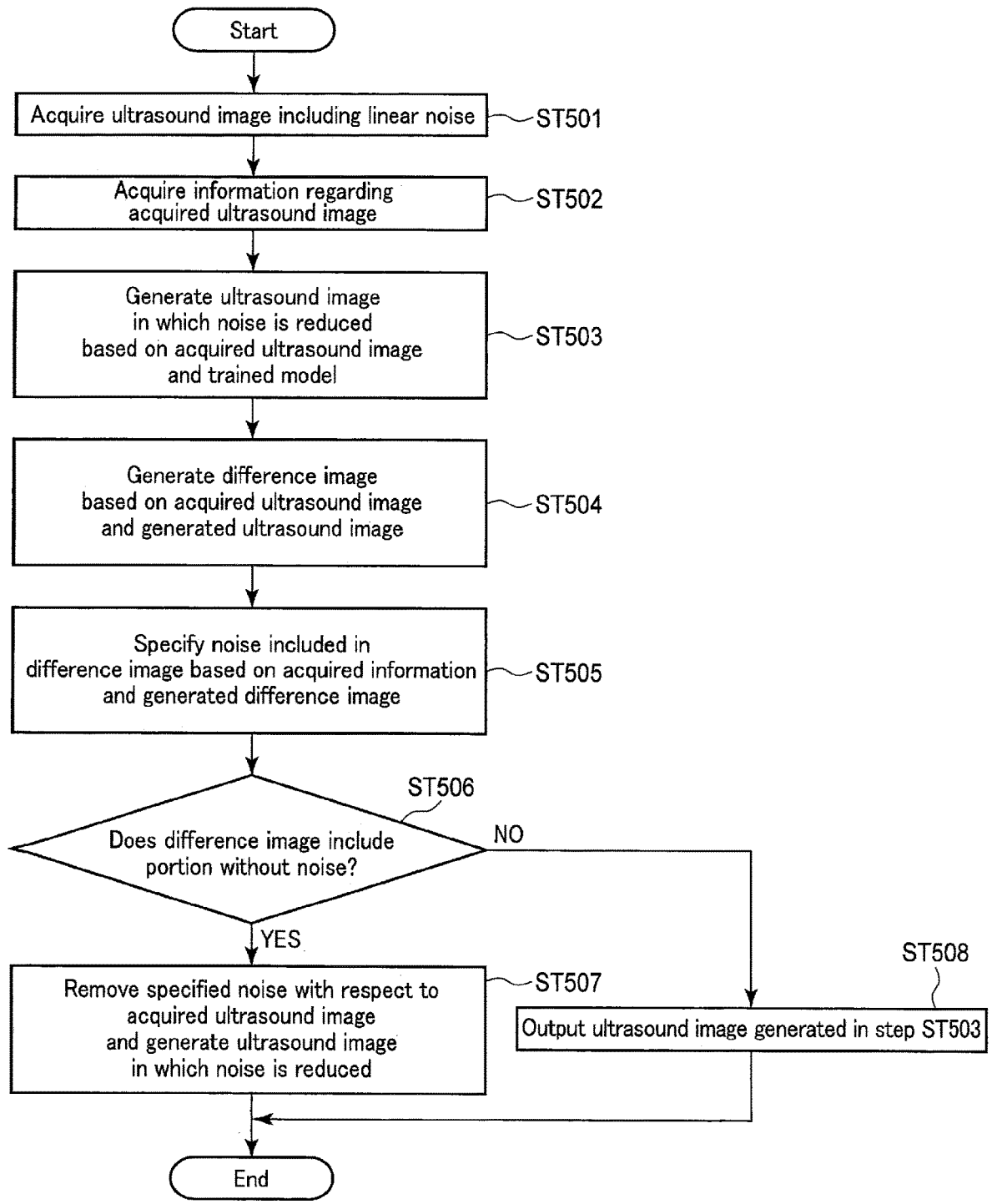
FIG. 18 is a flowchart explaining an operation of the medical image processing apparatus according to the fifth embodiment.
Figure 19:
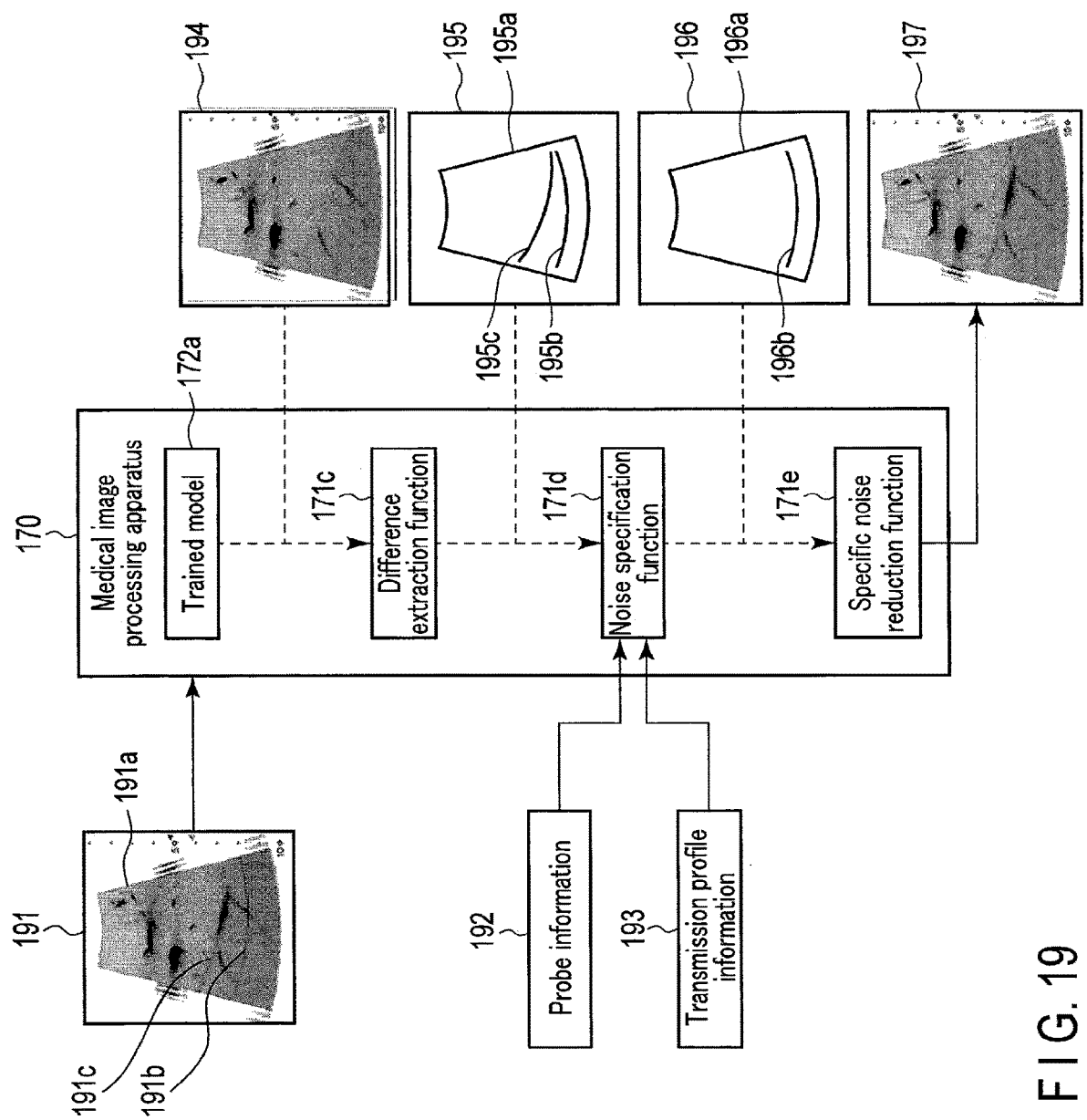
FIG. 19 is a drawing schematically showing an operation of the medical image processing apparatus according to the fifth embodiment.

The operation of the medical image processing apparatus 170 according to the fifth embodiment configured in the above manner will now be explained in accordance with the processing procedure of processing circuitry 171. Hereinafter, explanations will be made by using the flowchart of FIG. 18, and the schematic view of FIG. 19. FIG. 18 is a flowchart explaining the operation of the medical image processing apparatus according to the fifth embodiment. FIG. 19 is a drawing schematically showing the operation of the medical image processing apparatus according to the fifth embodiment.

The flowchart of FIG. 18 starts by the processing circuitry 171 executing the noise reduction program, which, for example, is triggered by an instruction to activate an application relating to the noise reduction processing input by the operator operating the terminal device.

(Step ST501)

When the noise reduction program is executed, the processing circuitry 171 executes the acquisition function 171a. When the acquisition function 171a is executed, the processing circuitry 171 acquires an ultrasound image including linear noise that is designated by the operator from the medical image management system. The ultrasound image to be acquired corresponds to, for example, an ultrasound image 191 of FIG. 19. The ultrasound image 191 has arc noise 191b in a drawing region 191a. Furthermore, the ultrasound image 191 includes an arcuate abdominal wall 191c.

(Step ST502)

The processing circuitry 171 then acquires information on the acquired ultrasound image by the acquisition function 171a. Specifically, the processing circuitry 171 acquires probe information and transmission profile information relating to the acquired ultrasound image. For example, probe information 192 and transmission profile information 193 are attached to the ultrasound image 191 of FIG. 19.

(Step ST503)

After acquiring the ultrasound image, the probe information, and the transmission profile information, the processing circuitry 171 executes the noise reduction function 171b. When the noise reduction function 171b is executed, the processing circuitry 171 generates the ultrasound image in which noise is reduced based on the acquired ultrasound image and a trained model. The ultrasound image to be generated corresponds to, for example, an ultrasound image 194 of FIG. 19. The ultrasound image 194 is obtained by reducing the arc noise 191b and the abdominal wall 191c in the ultrasound image 191.

For example, the processing circuitry 171 generates the ultrasound image 194 based on the ultrasound image 191 and the trained model 172a.

(Step ST504)

After generating the ultrasound image in which noise is reduced, the processing circuitry 171 executes the difference extraction function 171c. When the difference extraction function 171c is executed, based on the acquired ultrasound image and the generated ultrasound image, the processing circuitry 171 generates a difference image from which the reduced noise is extracted. Specifically, by extracting the difference between the acquired ultrasound image and the generated ultrasound image, the processing circuitry 171 generates the difference image from which the reduced noise is extracted.

The difference image to be generated corresponds to, for example, a difference image 195 of FIG. 19. The difference image 195 corresponds to, for example, mask data, and includes an extraction line 195b and an extraction line 195c in a drawing region 195a. The extraction line 195b corresponds to the arc noise 191b, and the extraction line 195c corresponds to the abdominal wall 191c.

Specifically, by extracting the difference between the ultrasound image 191 and the ultrasound image 194, the processing circuitry 171 generates the difference image 195.

(Step ST505)

After generating the difference image, the processing circuitry 171 executes the noise specification function 171d. By executing the noise specification function 171d, the processing circuitry 171 specifies the noise included in the difference image based on the acquired information and the generated difference image. Specifically, the processing circuitry 171 specifies the noise included in the difference image based on the acquired probe information and transmission profile information, and the generated difference image. The processing circuitry 171 may also generate a noise specified image including the specified noise.

The generated noise specified image corresponds to, for example, a noise specified image 196 of FIG. 19. The noise specified image 196 has arc noise 196b indicating position information of the linear noise in a drawing region 196a.

For example, the processing circuitry 171 specifies the noise included in the difference image 195 based on the probe information 192, the transmission profile information 193, and the difference image 195, and generates the noise specified image 196.

(Step ST506)

In the case where the difference image includes a portion that is not noise, the processing circuitry 171 performs the processing of the specified noise reduction function 171e with respect to the acquired ultrasound image. Here, the processing proceeds to step ST507.

On the other hand, in the case where the difference image does not include a portion that is not noise, the processing circuitry 171 does not perform the processing of the specified noise reduction function 171e with respect to the acquired ultrasound image. Here, the processing proceeds to step ST508.

(Step ST507)

After the noise is specified, the processing circuitry 171 executes the specified noise reduction function 171e. When the specified noise reduction function 171e is executed, the processing circuitry 171 reduces the specified noise with respect to the acquired ultrasound image, and generates an ultrasound image in which the noise is reduced. Specifically, by reducing the noise portion specified by the noise specification image in the acquired ultrasound image by the filter processing, the processing circuitry 171 generates an ultrasound image in which the noise is reduced. The ultrasound image to be generated corresponds to, for example, an ultrasound image 197 of FIG. 19.

For example, by reducing the arc noise 196b specified by the noise specification image 196 in the ultrasound image 191 by the filter processing, the processing circuitry 171 generates the ultrasound image 197 in which the arc noise 191b is reduced.

After step ST507, the processing circuitry 171 stores the generated ultrasound image in the medical image management system, displays the generated ultrasound image on a display of the terminal device, and ends the noise reduction program.

(Step ST508)

After the noise is specified, the processing circuitry 171 outputs the ultrasound image generated in step ST503. Specifically, the processing circuitry 171 stores the generated ultrasound image in the medical image management system, displays the generated ultrasound image on a display of the terminal device, and ends the noise reduction program.

As explained above, the medical image processing apparatus according to the fifth embodiment acquires an ultrasound image including linear noise and information regarding the ultrasound image, and generates an ultrasound image in which noise is reduced by inputting the acquired ultrasound image to a trained model that generates an ultrasound image in which the noise is reduced based on the ultrasound image including linear noise. The medical image processing apparatus generates a difference image from which the reduced noise is extracted based on the acquired ultrasound image and the generated ultrasound image, and specifies the noise included in the difference image based on the acquired information and the difference image. In the case where the difference image includes a portion that is not specified noise, the medical image processing apparatus generates an ultrasound image in which the specified noise is reduced with respect to the acquired ultrasound image.

Accordingly, the present medical image processing apparatus is capable of preventing a portion that is not noise from being reduced, and reducing only the noise in accordance with the wavefront shape of the transmission wave occurring in the ultrasound image.

Furthermore, the present medical image processing apparatus is capable of using the probe information and the transmission profile information as the acquired information. The present medical image processing apparatus is also capable of using an ultrasound image including noise in accordance with the wavefront shape of the transmission wave. The present medical image processing apparatus is also capable of using an ultrasound image including noise in accordance with the wavefront shape of the transmission wave, which is a plane wave, a diffusion wave, or a focusing wave.

(Modification of Fifth Embodiment)

The medical image processing apparatus according to the fifth embodiment generates an ultrasound image after performing noise reduction by the noise reduction processing using a trained model, and generates a difference image between the ultrasound images before and after the noise reduction. On the other hand, a medical image processing apparatus according to a modification of the fifth embodiment generates a difference image by using a trained model for generating the difference image.

The trained model according to the present modification is a trained machine learning model that is obtained by performing machine learning on a machine learning model in accordance with a model learning program based on training data. Here, the trained model of the present modification is provided with a function to output a difference image from which a noise portion is extracted based on an input of an ultrasound image that includes linear noise. In this case, the training data includes input data, which is an ultrasound image including linear noise, and output data, which is a difference image from which a noise portion is extracted. The training data according to the present modification is, for example, a combination of the ultrasound image 191 and the difference image 195 of FIG. 19.

Therefore, the medical image processing apparatus according to the modification of the fifth embodiment acquires an input image based on reception data collected by transmitting/receiving ultrasound, and generates an output image by inputting the input image to the trained model for generating, based on an input image, a difference image (an output image) in which a noise portion is extracted from an input image.

Accordingly, the present medical image processing apparatus is capable of directly generating a difference image from which a noise portion is extracted without having to generate the ultrasound images before and after the noise reduction, respectively.

Sixth Embodiment

Each configuration of one of the medical image processing apparatuses according to the first embodiment and the third embodiment to the fifth embodiment, and the model learning apparatus according to the second embodiment may be incorporated into an ultrasound diagnosis apparatus. That is, the ultrasound diagnosis apparatus may include each function of the above medical image processing apparatuses and the model learning apparatus. In the following, for example, a case in which the medical image processing apparatus according to the first embodiment comprises a configuration of an ultrasound diagnosis apparatus will be explained.

FIG. 20 is a block diagram showing a configuration example of an ultrasound diagnosis apparatus according to a sixth embodiment. As shown in FIG. 20, for example, an ultrasound diagnostic apparatus 200 according to the present embodiment comprises an apparatus main body 210 and an ultrasound probe 220. The apparatus main body 210 is connected to an external apparatus 230 via a network (NW). The apparatus main body 210 is also connected to a display device 240 and an input device 250. The external apparatus 230 corresponds to, for example, the terminal device 2 and the medical image management system 3 of FIG. 1.

The apparatus main body 210 comprises ultrasound transmission circuitry 211, ultrasound reception circuitry 212, internal storage circuitry 213, an image memory 214, an input interface 215, a communication interface 216, and processing circuitry 217.

The internal storage circuitry 213 stores a system control program of the ultrasound diagnostic apparatus 200, instructions of an operator transmitted from the input device 250, and various data received via the NW, etc. The internal storage circuitry 213 also stores a trained model 213a. The internal storage circuitry 213 may store the trained model 213a in advance of delivery of the ultrasound diagnosis apparatus 200. Alternatively, the internal storage circuitry 213 may store the trained model 213a acquired from a server device, etc. (not shown) after the ultrasound diagnosis apparatus 200 is delivered. Since the trained model 213a is similar to the trained model 12a of FIG. 1, explanations thereof will be omitted.

The internal storage circuitry 213 is a storage device, such as a ROM, a RAM, an HDD, an SSD, or an integrated circuit storage device, storing various information, and stores, for example, the system control program and the trained model 213a.

The processing circuitry 217 comprises, as hardware resources, a processor and a memory. The processing circuitry 217 reads the system control program stored in the internal storage circuitry 213 in accordance with an instruction input by an operator via the input device 250, etc. The processing circuitry 217 executes each function to acquire an ultrasound image in accordance with the read system control program. Each of the above functions is, for example, a B mode processing function 217a, a Doppler processing function 217b, an image generating function 217c, an image processing function 217d, a display control function 217g, and a system control function 217h. The processing circuitry 217 generates the ultrasound image by the image generating function 217c.

The processing circuitry 217 also executes each function relating to noise reduction processing in accordance with the read system control program. Each of the above functions is, for example, an acquisition function 217e (acquisition unit) and a noise reduction function 217f. Since the acquisition function 217e and the noise reduction function 217f are similar to the acquisition function 11a and the noise reduction function 11b of FIG. 1, explanations thereof will be omitted. The processing circuitry 217 that executes the acquisition function 217e may be referred to as an "acquisition unit", and the processing circuitry 217 that executes the noise reduction function 217f may be referred to as a "processing unit".

The ultrasound probe 220 emits ultrasound with respect to a subject P, and receives reflected waves of the emitted ultrasound. In other words, the ultrasound probe 220 collects reception data by transmitting/receiving the ultrasound. Therefore, an ultrasound image generated by the image generating function 217c may be referred to as "an input image based on reception data collected by transmitting/receiving ultrasound".

The ultrasound probe 220 includes a plurality of vibration elements driven in accordance with a delay profile. Furthermore, various types of probes may be used as the ultrasound probe 220. Therefore, by the noise reduction function 217f, the processing circuitry 217 may also generate an output image by inputting an input image to a trained model according to at least one of the type of ultrasound probe or the delay profile.

As explained above, the ultrasound diagnosis apparatus according to the sixth embodiment includes each configuration of one of the medical image processing apparatuses according to the first embodiment and the third embodiment to the fifth embodiment, or the training data producing apparatus according to the second embodiment.

Therefore, in the case of including each configuration of one of the medical image processing apparatuses according to the first embodiment and the third to the fifth embodiments, the present ultrasound diagnosis apparatus is capable of reducing linear noise that is generated by using a transmission wave caused by a plane wave or a diffusion wave. Furthermore, in the case of including each configuration of the training data producing apparatus according to the second embodiment, the present ultrasound diagnosis apparatus is capable of producing the training data to be used for the trained model for reducing linear noise that is generated by using a transmission wave caused by a plane wave or a diffusion wave.

Application Example

One of the medical image processing apparatuses according to the first embodiment and the third to fifth embodiments may include an attachment function (an attachment unit) to attach information indicating the delay profile to the reception data or the ultrasound image based on the reception data in each processing circuitry.

Processing circuitry according to the present application example attaches, by an attachment function, information indicating a delay profile, which was applied when transmitting ultrasound, to reception data collected by transmitting/receiving the ultrasound, or to an ultrasound image based on the reception data. Specifically, the processing circuitry attaches the information indicating the delay profile to the ultrasound image by using an ultrasound image acquired by an acquisition function and the information indicating the delay profile. The attachment function according to the present application example may also be included in processing circuitry or control circuitry included in the medical image management system 3.

Therefore, a medical image processing apparatus according to the present application example comprises an attachment unit that attaches information indicating the delay profile, which was applied when transmitting ultrasound, to the reception data collected by transmitting/receiving the ultrasound, or to the ultrasound image based on the reception data.

Accordingly, the present medical image processing apparatus is capable of attaching information indicating the delay profile to the ultrasound image.

According to at least one of the above-explained embodiments, it is possible to reduce noise in accordance with the wavefront shape of the transmission wave.

The term "processor" used in each of the above embodiments means, for example, a circuit such as a central processing unit (CPU), a graphics processing unit (GPU), an ASIC, or a programmable logic device (for example, a simple programmable logic device (SPLD), a complex programmable logic device (CPLD), and an FPGA).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus, comprising processing circuitry configured to:
acquire an input image based on reception data collected by transmitting/receiving ultrasound by using an ultrasound probe including a plurality of vibration elements driven in accordance with a delay profile;
store a plurality of trained models for generating, based on the input image, an output image in which noise is reduced according to a wavefront shape of when the ultrasound is transmitted in the input image;
select a trained model corresponding to a type of the ultrasound probe or the delay profile from the plurality of trained models; and
generate an output image by inputting the input image to the selected trained model.

2. The medical image processing apparatus according to claim 1, wherein the processing circuitry is further configured to generate the output image by the trained model according to the wavefront shape.

3. The medical image processing apparatus according to claim 1, wherein the processing circuitry is further configured to determine the trained model based on supplementary information indicating at least one of the type of the ultrasound probe or the delay profile, which is attached to the reception data or the input image.

4. The medical image processing apparatus according to claim 1, wherein the trained model is a model that is trained by using a first image, which is an ultrasound image, and a second image, which is obtained by adding a straight linear picture or an arcuate picture to the first image.

5. The medical image processing apparatus according to claim 4, wherein the first image is a B mode image expressing intensity of the received ultrasound by luminance, and the second image is an image in which the picture is added to include a pixel with relatively high luminance among pixel groups configuring the first image.

6. A medical image processing apparatus, comprising processing circuitry configured to attach information indicating a delay profile, which was applied when transmitting ultrasound, to reception data collected by transmitting/receiving the ultrasound, or to an ultrasound image based on the reception data,
wherein the delay profile is for use by the medical image processing apparatus of claim 1.

7. A training data producing apparatus, comprising processing circuitry configured to:
acquire an ultrasound image and mask data indicating a picture of a straight linear or an arcuate;
perform processing to add the picture to the ultrasound image by using the mask data; and
output the ultrasound image and a processed ultrasound image as training data to be used for a machine learning model.

8. An ultrasound diagnosis apparatus, comprising processing circuitry configured to:
generate, as an input image, an ultrasound image based on reception data collected by transmitting/receiving ultrasound by using an ultrasound probe including a plurality of vibration elements driven in accordance with a delay profile;
store a plurality of trained models for generating, based on the input image, an output image in which noise is reduced according to a wavefront shape of when the ultrasound is transmitted in the input image;
select a trained model corresponding to a type of the ultrasound probe or the delay profile from the plurality of trained models; and
generate an output image by inputting the input image to the selected trained model.

* * * * *